US 8,198,600 B2

(12) United States Patent
Neustadter et al.

(10) Patent No.: US 8,198,600 B2
(45) Date of Patent: Jun. 12, 2012

(54) LOCALIZATION OF A RADIOACTIVE SOURCE

(75) Inventors: David Maier Neustadter, Natania (IL); Giora Kornblau, Binyamina (IL)

(73) Assignee: Navotek Medical Ltd., Yokneam (IL)

( * ) Notice: Subject to any disclaimer, the term of this patent is extended or adjusted under 35 U.S.C. 154(b) by 0 days.

(21) Appl. No.: 13/091,775

(22) Filed: Apr. 21, 2011

(65) Prior Publication Data

US 2011/0198510 A1 Aug. 18, 2011

Related U.S. Application Data

(60) Division of application No. 11/990,315, filed as application No. PCT/IB2006/052770 on Aug. 10, 2006, now Pat. No. 7,952,079, which is a continuation-in-part of application No. PCT/IL2005/000871, filed on Aug. 11, 2005.

(60) Provisional application No. 60/773,931, filed on Feb. 16, 2006, provisional application No. 60/804,178, filed on Jun. 8, 2006, provisional application No. 60/773,930, filed on Feb. 16, 2006, provisional application No. 60/600,725, filed on Aug. 12, 2004, provisional application No. 60/619,792, filed on Oct. 19, 2004, provisional application No. 60/619,897, filed on Oct. 19, 2004.

(30) Foreign Application Priority Data

Oct. 19, 2005 (WO) .................. PCT/IL2005/001101
Aug. 10, 2006 (WO) .................. PCT/IB2006/052771

(51) Int. Cl.
*A61B 19/00* (2006.01)
*A61B 6/12* (2006.01)

(52) U.S. Cl. ..... 250/393; 250/394; 250/395; 250/336.1; 250/493.1; 250/498.1; 600/3; 600/424; 600/425

(58) Field of Classification Search .................. 250/393, 250/394, 395, 493.1; 600/3, 424, 425
See application file for complete search history.

(56) References Cited

U.S. PATENT DOCUMENTS 3,777,148 A 12/1973 Miraldi
(Continued)

FOREIGN PATENT DOCUMENTS

CN 1469720 1/2004
(Continued)

OTHER PUBLICATIONS

"Calypso® 4D Localization System-Gps for the Body®" in Calypso® Medical: Products & Technology -The Problem, downloaded from <http://calypsomedical.com/products/> on Dec. 12, 2002 (4 pages).

(Continued)

*Primary Examiner* — David A Vanore
(74) *Attorney, Agent, or Firm* — Finnegan, Henderson, Farabow, Garrett & Dunner, L.L.P.

(57) ABSTRACT

An angle-responsive sensor, comprising: a radiation detector adapted to detect ionizing radiation; at least one collimator arranged to block radiation from reaching the detector in a manner dependent on a relative orientation of a radiation source, the detector and the collimator, the detector and the collimator defining an aim for the sensor; and circuitry coupled to the detector and which generates an output signal which varies as a function of the relative orientation, wherein the detector and the collimator are arranged to have a working volume of at least 10 cm in depth and having an angular width, such that the slope of the signal as a function of angle varies by less than a factor of 2 over the working volume.

20 Claims, 21 Drawing Sheets

U.S. PATENT DOCUMENTS

| | | | |
|---|---|---|---|
| 3,794,840 A | 2/1974 | Scott | |
| 3,951,550 A | 4/1976 | Slick | |
| 4,096,862 A * | 6/1978 | DeLuca | 600/433 |
| 4,123,654 A | 10/1978 | Reiss et al. | |
| 4,193,689 A | 3/1980 | Reymond et al. | |
| 4,209,700 A * | 6/1980 | Stoddart | 250/363.04 |
| 4,215,694 A | 8/1980 | Isakov et al. | |
| 4,243,652 A | 1/1981 | Francis | |
| 4,250,392 A | 2/1981 | Leask et al. | |
| 4,636,380 A | 1/1987 | Wong | |
| 4,755,680 A | 7/1988 | Logan | |
| 4,782,840 A | 11/1988 | Martin, Jr. et al. | |
| 4,857,729 A | 8/1989 | Gadeken et al. | |
| 4,944,754 A | 7/1990 | Linkow et al. | |
| 4,959,547 A | 9/1990 | Carroll et al. | |
| 5,114,401 A | 5/1992 | Stuart et al. | |
| 5,170,055 A | 12/1992 | Carroll et al. | |
| 5,207,223 A | 5/1993 | Adler | |
| 5,211,165 A | 5/1993 | Dumoulin et al. | |
| 5,342,283 A | 8/1994 | Good | |
| 5,344,452 A | 9/1994 | Lemperle | |
| 5,345,084 A | 9/1994 | Byrd | |
| 5,460,592 A | 10/1995 | Langton et al. | |
| 5,665,970 A | 9/1997 | Kronenberg et al. | |
| 5,694,933 A | 12/1997 | Madden et al. | |
| 5,707,332 A | 1/1998 | Weinberger | |
| 5,740,808 A | 4/1998 | Panescu et al. | |
| 5,813,985 A | 9/1998 | Carroll | |
| 5,846,513 A | 12/1998 | Carroll et al. | |
| 5,848,967 A | 12/1998 | Cosman | |
| 5,933,517 A | 8/1999 | Grangeat et al. | |
| 5,938,602 A | 8/1999 | Lloyd | |
| 5,961,451 A | 10/1999 | Reber et al. | |
| 5,961,457 A | 10/1999 | Raylman et al. | |
| 5,961,458 A | 10/1999 | Carroll | |
| 5,987,350 A | 11/1999 | Thurston | |
| 6,016,439 A | 1/2000 | Acker | |
| 6,033,721 A | 3/2000 | Nassuphis | |
| 6,068,623 A | 5/2000 | Zadno-Azizi et al. | |
| 6,100,530 A | 8/2000 | Kronenberg et al. | |
| 6,188,355 B1 | 2/2001 | Gilboa | |
| 6,230,038 B1 * | 5/2001 | von Gutfeld et al. | 600/409 |
| 6,261,243 B1 | 7/2001 | Burney et al. | |
| 6,264,599 B1 | 7/2001 | Slater et al. | |
| 6,275,724 B1 | 8/2001 | Dickinson et al. | |
| 6,332,089 B1 | 12/2001 | Acker et al. | |
| 6,363,940 B1 | 4/2002 | Krag | |
| 6,371,904 B1 | 4/2002 | Sirimanne et al. | |
| 6,380,732 B1 | 4/2002 | Gilboa | |
| 6,402,677 B1 | 6/2002 | Jacobs | |
| 6,419,621 B1 | 7/2002 | Sioshansi et al. | |
| 6,427,314 B1 | 8/2002 | Acker | |
| 6,436,026 B1 | 8/2002 | Sioshansi et al. | |
| 6,455,856 B1 | 9/2002 | Gagnon | |
| 6,496,717 B2 | 12/2002 | Cox et al. | |
| 6,510,336 B1 | 1/2003 | Daghighian et al. | |
| 6,558,612 B1 | 5/2003 | Hubbard | |
| 6,580,938 B1 | 6/2003 | Acker | |
| 6,593,884 B1 * | 7/2003 | Gilboa et al. | 342/448 |
| 6,603,124 B2 | 8/2003 | Maublant | |
| 6,618,612 B1 | 9/2003 | Acker et al. | |
| 6,675,810 B2 | 1/2004 | Krag | |
| 6,690,963 B2 | 2/2004 | Ben-Haim et al. | |
| 6,696,686 B1 | 2/2004 | Wainer et al. | |
| 6,698,433 B2 | 3/2004 | Krag | |
| 6,711,429 B1 | 3/2004 | Gilboa et al. | |
| 6,749,555 B1 | 6/2004 | Winkler et al. | |
| 6,750,020 B2 | 6/2004 | Shuber | |
| 6,751,492 B2 | 6/2004 | Ben-Haim | |
| 6,788,967 B2 | 9/2004 | Ben-Haim et al. | |
| 6,812,842 B2 | 11/2004 | Dimmer | |
| 6,822,570 B2 | 11/2004 | Dimmer et al. | |
| 6,838,990 B2 | 1/2005 | Dimmer | |
| 6,847,838 B1 * | 1/2005 | Macey et al. | 600/431 |
| 6,889,833 B2 | 5/2005 | Seiler et al. | |
| 6,918,919 B2 | 7/2005 | Krag | |
| 6,920,347 B2 | 7/2005 | Simon et al. | |
| 6,937,696 B1 | 8/2005 | Mostafavi | |
| 6,977,504 B2 | 12/2005 | Wright et al. | |
| 7,047,063 B2 | 5/2006 | Burbank et al. | |
| 7,066,924 B1 | 6/2006 | Garibaldi et al. | |
| 7,247,160 B2 | 7/2007 | Seiler et al. | |
| 7,289,839 B2 | 10/2007 | Dimmer et al. | |
| 7,407,054 B2 | 8/2008 | Seiler et al. | |
| 7,684,849 B2 | 3/2010 | Wright et al. | |
| 2001/0005930 A1 | 7/2001 | Coniglione | |
| 2002/0058853 A1 | 5/2002 | Kaplan | |
| 2002/0061298 A1 | 5/2002 | Coffey et al. | |
| 2002/0077533 A1 | 6/2002 | Bieger et al. | |
| 2002/0087078 A1 | 7/2002 | Cox et al. | |
| 2002/0193685 A1 | 12/2002 | Mate et al. | |
| 2003/0036700 A1 | 2/2003 | Weinberg | |
| 2003/0088140 A1 | 5/2003 | Terwilliger et al. | |
| 2003/0111611 A1 | 6/2003 | Maublant | |
| 2003/0192557 A1 | 10/2003 | Krag et al. | |
| 2004/0015075 A1 | 1/2004 | Kimchy et al. | |
| 2004/0034297 A1 | 2/2004 | Darrow et al. | |
| 2004/0037394 A1 | 2/2004 | Kuroda et al. | |
| 2004/0054248 A1 | 3/2004 | Kimchy | |
| 2004/0068157 A1 | 4/2004 | Gellman et al. | |
| 2004/0073107 A1 | 4/2004 | Sioshansi et al. | |
| 2004/0116767 A1 | 6/2004 | Lebovic et al. | |
| 2004/0199072 A1 | 10/2004 | Sprouse et al. | |
| 2004/0236213 A1 | 11/2004 | Jones et al. | |
| 2005/0010099 A1 | 1/2005 | Raabe et al. | |
| 2005/0027196 A1 | 2/2005 | Fitzgerald | |
| 2005/0054910 A1 | 3/2005 | Tremblay et al. | |
| 2005/0055174 A1 | 3/2005 | David et al. | |
| 2005/0085717 A1 | 4/2005 | Shahidi | |
| 2005/0197564 A1 | 9/2005 | Dempsey | |
| 2005/0245814 A1 | 11/2005 | Anderson et al. | |
| 2005/0261570 A1 | 11/2005 | Mate et al. | |
| 2007/0055090 A1 | 3/2007 | Neustadter et al. | |
| 2007/0055144 A1 | 3/2007 | Neustadter et al. | |
| 2007/0205373 A1 * | 9/2007 | Kornblau et al. | 250/390.12 |
| 2007/0265491 A1 | 11/2007 | Krag et al. | |
| 2008/0262473 A1 * | 10/2008 | Kornblau et al. | 604/529 |
| 2009/0127459 A1 * | 5/2009 | Neustadter et al. | 250/336.1 |
| 2009/0131734 A1 | 5/2009 | Neustadter et al. | |

FOREIGN PATENT DOCUMENTS

| | | |
|---|---|---|
| EP | 0273257 | 7/1988 |
| EP | 0466681 | 4/1992 |
| EP | 0531081 | 3/1993 |
| EP | 0993843 | 4/2000 |
| EP | 1034738 | 9/2000 |
| EP | 1060764 | 12/2000 |
| FR | 1561351 | 3/1969 |
| GB | 2330263 | 4/1999 |
| JP | 01-288250 | 11/1989 |
| WO | WO 97/29699 | 8/1997 |
| WO | WO 97/29700 | 8/1997 |
| WO | WO 99/21615 | 5/1999 |
| WO | WO 99/35966 | 7/1999 |
| WO | WO 00/24332 | 5/2000 |
| WO | WO 00/57923 | 10/2000 |
| WO | WO 00/71204 | 11/2000 |
| WO | WO 01/30447 | 5/2001 |
| WO | WO 01/54765 | 8/2001 |
| WO | WO 01/87409 | 11/2001 |
| WO | WO 02/16965 | 2/2002 |
| WO | WO 02/39142 | 5/2002 |
| WO | WO 02/39917 | 5/2002 |
| WO | WO 02/39918 | 5/2002 |
| WO | WO 02/078785 | 10/2002 |
| WO | WO 03/011161 | 2/2003 |
| WO | WO 03/032837 | 4/2003 |
| WO | WO 2004/026111 | 4/2004 |
| WO | WO 2006/004542 | 1/2006 |
| WO | WO 2006/016368 | 2/2006 |
| WO | WO 2006/043276 | 4/2006 |
| WO | WO 2007/017846 | 2/2007 |
| WO | WO 2007/017847 | 2/2007 |
| WO | WO 2007/094001 | 8/2007 |
| WO | WO 2007/094002 | 8/2007 |

OTHER PUBLICATIONS

Hyun an et al. "Optimization of a Table-Top Compton Camera System by Monte Carlo Simulation", Nuclear Instruments and Methods in Physics Research a, 580: 169-172, 2007 (4 pages).

Kirsch et al. "Real Time Tracking of Tumor Positions for Precision Irradiation", Car'98, Computer Assisted Radiology and Surgery, Proceedings of the International Congress and Exhibition, Proceedings of the International Symposium on Computer Assisted Radiology and Surgery, P.262-264, 1998 (3 pages).

Lengyel J. et al., "Three-dimensional reconstruction and vol. rendering of intravascular ultrasound slices imaged on a curved arterial path"; in Nicholas Ayache, editor, Computer Vision, Virtual Reality and Robotics in Medicine, Lecture Notes in Computer Science. Springer-Verlag, Apr. 1995, pp. 399-405 (7 pages).

Singh "An Electronically Collimated gamma Camera for single Photon Emission Computed Tomography. Part I: Theoretical Considerations and Design Criteria", Medical Physics, 10: 421-427, 1983 (7 pages).

Invitation to pay Additional Fees mailed Jan. 4, 2007, from the International Searching Authority in Application No. PCT/IB2006/052770 (5 pages).

International Search Report mailed May 23, 2007, from the International Searching Authority in Application No. PCT/IB2006/052770 (7 pages).

Revised International Search Report mailed Sep. 11, 2007, from the International Searching Authority in Application No. PCT/IB2006/052770 (6 pages).

Written Opinion completed Sep. 11, 2007, from the International Searching Authority in Application No. PCT/IB2006/052770 (12 pages).

Invitation to restrict or Pay Additional Fees, and, whereapplicable, Protest Fee, mailed Jan. 29, 2008, from the International Searching Authority in Application No. PCT/IB2006/052770, including claim set received at the EPO on Dec. 10, 2007 (9 pages).

Feb. 7, 2008 Letter from Ehrlich & Fenster to European Patent Office regarding Application No. PCT/1B2006/052770, including claim set (11 pages total).

Notification Concerning Informal Communication with the Applicant mailed Feb. 8, 2008, from the International Preliminary Examining Authority in Application No. PCT/IB2006/052770 (3 pages).

International Preliminary Report on Patentability mailed Feb. 21, 2008, from the International Preliminary Examining Authority in Application No. PCT/IB2006/052770, including claims Annex (19 pages).

Communication from the European Patent Office dated Aug. 6, 2008 in Application No. 06795628.4 (4 pages).

Office Action dated May 4, 2010, in the Israel Patent Office for Israel Application No. 189442 including excerpts from WO 02/16965 A2 (8 pages, including translation).

International Search Report mailed Mar. 6, 2007, from the International Searching Authority in Application No. PCT/IL05/00871 (3 pages).

Written Opinion mailed Mar. 6, 2007, from the International Searching Authority in Application No. PCT/IL05/00871 (5 pages).

International Preliminary Report on Patentability issued Apr. 3, 2007, from the International Bureau of WIPO in Application No. PCT/IL2005/000871 (6 pages).

International Preliminary Report on Patentability with completion date Mar. 25, 2008, from the International Preliminary Examining Authority in Application No. PCT/IL05/00871, including claim Annex (9 pages).

Extended European Search Report and Written Opinion dated May 7, 2010, for European Application No. 05770170.8 (11 pages).

Office Action dated Feb. 25, 2010, in the Israel Patent Office for Israel Application No. 181261, including excerpts from U.S. Appl. No. 4/123,654 and EP 1034738 (13 pages, including translation).

Office Action dated Oct. 24, 2010, in the Israel Patent Office for Israel Application No. 181261, including excerpts from U.S. Patent No. 6,696,686, U.S. Pat. Pub. 2004/0037394, and U.S. Pat. Pub. 2004/0054248 (19 pp., including translation).

Office Action dated Jan. 12, 2011, in the Israel Patent Office for Israel Application No. 207209 including excerpts from US-2003/0111611 (6 pp., including translation).

Office Action dated Jan. 16, 2011, in the Israel Patent Office for Israel Application No. 207210 including excerpts from US 3,951,550 (7 pp., including translation).

Office Action dated Oct. 27, 2009, in the Instituto Mexicano de la Propriedad Industrial for Mexican Application No. Mx/a/2007/001783 (5 pp., including English-language summary).

Office Action dated Feb. 8, 2010, in the Instituto Mexicano de la Propriedad Industrial for Mexican Application No. Mx/a/2007/001783 (6 pp., including summary translation).

Translation of Office Action dated Aug. 7, 2009, from the State Intellectual Property Office of the People's Republic of China in Application No. 200580034274.1 (9 pp.).

Translation of Second Office Action dated Sep. 27, 2010, in the State Intellectual Property Office of the People's Republic of China for Chinese Application No. 200580032474.1 (4 pp.).

Uspto Office Action mailed Jun. 24, 2009, in U.S. Application No. 10/599,963 (Now U.S. Patent No. 7,847,274) (5 pp.).

Uspto Office Action mailed Nov. 5, 2009, in U.S. Application No. 10/599,963 (Now U.S. Patent No. 7,847,274) (9 pp.).

Uspto Office Action mailed Apr. 22, 2010, in U.S. Application No. 10/599,963 (Now U.S. Patent No. 7,847,274) (10 pp.).

Uspto Advisory Acton mailed Jun. 22, 2010, in U.S. Application No. 10/599,963 (Now U.S. Patent No. 7,847,274) (2 pp.).

Uspto Notice of Allowability mailed Jul. 30, 2010, in U.S. Application No. 10/599,963 (Now U.S. Patent No. 7,847,274) (3 pp.).

Second Preliminary Amendment dated Jul. 26, 2007, in U.S. Application No. 11/635,441 to Krag et al. (7 pp.).

Preliminary Amendment dated Sep. 26, 2008, in U.S. Application No. 11/635,441 to Krag et al. (8 pp.).

Uspto Final Rejection mailed Feb. 3, 2011, in U.S. Application No. 11/635,441 to Krag et al. (13 pp.).

Uspto Examiner Interview Summary in U.S. Patent Application No. 11/635,441 with mail date Apr. 8, 2011 (4 pp. total).

Uspto Office Action mailed Apr. 13, 2010, in co-pending U.S. Application No. 11/463,664 (19 pp.).

USPTO Office Action mailed Oct. 15, 2010, in co-pending U.S. Appl. No. 11/463,664 (15 pages).

USPTO Office Action mailed Sep. 23, 2011, in U.S. Appl. No. 11/463,664 (15 pages total).

USPTO Office Action mailed Oct. 29, 2009, in co-pending U.S. Appl. No. 11/463,659 (6 pages).

USPTO Office Action mailed Apr. 27, 2010, in co-pending U.S. Appl. No. 11/463,659 (17 pages).

USPTO Office Action mailed Oct. 27, 2010, in co-pending U.S. Appl. No. 11/463,659 (13 pages).

USPTO Office Action mailed Feb. 18, 2011, in co-pending U.S. Application No. 11/463,659 (8 pp.). N/a.

USPTO Examiner Interview Summary in U.S. Appl. No. 11/463,659 with mail date Aug. 16, 2011 (2 pages total).

USPTO Final Office Action with mail date Nov. 4, 2011, in U.S. Appl. No. 11/463,659 (9 pages total).

USPTO Office Action with mail date May 2, 2011, in U.S. Appl. No. 12/917,052 (6 pages total).

USPTO Final Office Action with mail date May 5, 2011, in U.S. Appl. No. 12/697,160 (9 pages total).

International Search Report mailed May 30, 2006, from the International Searching Authority in Application No. PCT/IL05/01101 (2 pages).

International Preliminary Report on Patentability mailed May 9, 2007, from the International Preliminary Examining Authority in Application No. PCT/IL05/01101 (6 pages).

International Search Report mailed Jan. 3, 2007, from the International Searching Authority in Application No. PCT/IB2006/052771 (7 pages).

Written Opinion mailed Jan. 3, 2007, from the International Searching Authority in Application No. PCT/1B2006/052771 (7 pages).

International Preliminary Report on Patentability mailed Nov. 27, 2007, from the International Preliminary Examining Authority in Application No. PCT/IB2006/052771 with claims Annex (15 pages).

Invitation to Pay Additional Fees mailed Jan. 7, 2008, from the International Searching Authority in Application No. PCT/IL2007/000214 (7 pages).

International Search Report mailed Feb. 29, 2008, from the International Searching Authority in Application No. PCT/IL2007/000214 (8 pages).

Written Opinion mailed Feb. 29, 2008, from the International Searching Authority in Application No. PCT/IL2007/000214 (14 pages).

International Preliminary Report on Patentability with completion date Aug. 26, 2008, from the International Preliminary Examining Authority in Application No. PCT/IL2007/000214 with claims Annex (20 pages).

International Search Report mailed Jan. 7, 2008, from the International Searching Authority in Application No. PCT/IL2007/000215 (5 pages).

Written Opinion mailed Jan. 7, 2008, from the International Searching Authority in Application No. PCT/IL2007/000215 (8 pages).

International Preliminary Report on Patentability mailed Aug. 28, 2008, from the International Bureau of WIPO in Application No. PCT/IL2007/000215 (6 pages).

Woolfenden, J.M. et al., "Rapid in vivo localization of a lost brachytherapy seed," Medical Physics, vol. 11: 558-559, Jul./Aug. 1984 (2 pages).

* cited by examiner

LOCALIZATION OF A RADIOACTIVE SOURCE

RELATED APPLICATIONS

This Application is a divisional of U.S. patent application Ser. No. 11/990,315, filed Feb. 11, 2008 now U.S. Pat. No. 7,952,079, which is a National Phase of PCT Patent Application No. PCT/IB2006/052770, filed on Aug. 10, 2006 and claims the benefit of the filing date of U.S. Provisional Application Nos. 60/773,931 filed on Feb. 16, 2006, entitled "Radiation Oncology Application," 60/804,178 filed on Jun. 8, 2006, entitled "Radioactive Medical Implants," and 60/773,930 filed Feb. 16, 2006, entitled "Localization of a Radioactive Source," the disclosures of which are incorporated herein by reference.

PCT Patent Application No. PCT/IB2006/052770 is also a continuation-in-part of: PCT/IL2005/000871 filed on Aug. 11, 2005, entitled "Localization of a Radioactive Source within a Body of a Subject," which claims benefit of the filing date of U.S. Provisional Applications Nos. 60/600,725 filed on Aug. 12, 2004, entitled "Medical Navigation System Based on Differential Sensor," 60/619,792 filed on Oct. 19, 2004, entitled "Using a Catheter Or Guidewire Tracking System to Provide Positional Feedback for an Automated Catheter or Guidewire Navigation System," and 60/619,897 filed on Oct. 19, 2004, entitled "Using a Radioactive Source as the Tracked Element of a Tracking System." The disclosures of these applications are incorporated herein by reference.

This application is related to:

U.S. Provisional Application Nos. 60/619,898 filed on Oct. 19, 2004, entitled "Tracking a Catheter Tip by Measuring its Distance From a Tracked Guide Wire Tip";

International Patent Application PCT/IL2005/001101 filed on Oct. 19, 2005, entitled "Tracking a Catheter Tip by Measuring its Distance From a Tracked Guide Wire Tip";

International Patent Application PCT/IB2006/052771 filed on Aug. 10, 2006, entitled "Medical Treatment System and Method Using Radioactivity Based Position Sensor";

U.S. patent application Ser. No. 11/463,664 filed on Aug. 10, 2006, entitled "Medical Treatment System and Method";

U.S. patent application Ser. No. 11/463,659 filed on Aug. 10, 2006, entitled "Medical Treatment System and Method";

The disclosures of these applications are fully incorporated herein by reference.

FIELD OF THE INVENTION

The present invention relates to location and tracking of a source of ionizing radiation, for example within a body of a subject.

BACKGROUND OF THE INVENTION

Existing techniques for intrabody tracking include direct video imaging using a laparoscope; fluoroscopy (performance of the procedure under continuous or periodic X-Ray imaging); electromagnetic tracking, optical tracking, computerized tomography (CT) tracking and ultrasonic image assisted tracking. Some of these techniques explicitly avoid ionizing radiation. Those techniques which employ ionizing radiation, such as fluoroscopy and CT, require sufficient amounts of ionizing radiation that radiation exposure for subjects and medical staff is a subject of concern.

Some applications which require intrabody tracking, such as cardiac catheterization, typically use concurrently acquired images because the tissue through which the tracked medical device is being navigated moves frequently. Other applications which require intrabody tracking, such as intracranial procedures, are more amenable to the use of pre-acquired images because the relevant tissue is relatively static.

SUMMARY OF THE INVENTION

An aspect of some embodiments of the present invention relates to using ionizing radiation from a source in order to detect its position, optionally in or near the body of a subject, without production of an image. Optionally, the source is integrally formed with or attached to a medical device. Medical devices include, but are not limited to, tools, implants, navigational instruments and ducts.

In an exemplary embodiment of the invention, position of the source is determined by non-imaging data acquisition. For purposes of this specification and the accompanying claims, the phrase "non-imaging" indicates data acquired independent of an image acquisition process that includes the source and anatomical or other non-source features in a same image.

Optionally, position is determined using a sensor which has angular sensitivity resulting in a detectable change in output resulting from radiation detection according to an effective angle of incidence of radiation from the source. Greater sensitivity in effective angle of incidence provides greater efficiency of the position determination in terms of speed and accuracy. Embodiments with an angular range of less than ±100 milliradians, optionally less than ±50 milliradians are disclosed. In an exemplary embodiment of the invention, greater sensitivity to effective angle of incidence can be achieved by moving a radiation detector and/or a shield.

Optionally, the source of ionizing radiation has an activity in the range of 0.01 mCi to 0.5 mCi. Optionally, the source of ionizing radiation has an activity less than 0.1 mCi. Optionally, the source of ionizing radiation has an activity of about 0.05 mCi. In an exemplary embodiment of the invention, a radiation source which poses no significant health risk to a patient (i.e. short term exposure) and/or medical personnel (i.e. long term exposure) may be employed.

Optionally, the refresh rate for the location data insures that the locational information is temporally well correlated to the actual location of a tracked object (e.g. medical device). Recommended refresh rates vary according to the speed at which the tracked object moves and according to the environment in which the tracked object moves. In an exemplary embodiment of the invention, for tracking of medical devices through body parts which are more static, such as brain or digestive tract, lower refresh rates, for example 10 times/second may be adequate. In some embodiments for tracking of medical devices through body parts which move frequently, such as the heart, higher refresh rates, for example 20 times/second may be desirable. Optionally, gating to an ECG output may be implemented so that positions from selected cardiac cycle phases are plotted. Other exemplary refresh rates are higher than 30 Hz, and values intermediate 0.1 Hz, 1 Hz, 3 Hz, 10 Hz and 20 Hz.

Optionally, the RMS error of a calculated position of the source of ionizing radiation is less than 10 mm, optionally less than 5 mm, optionally less than 2 mm, optionally less than 1 mm, optionally 0.5 to 0.8 mm or better.

Variables which may influence the accuracy of determined position(s) include activity of the source in DPM, the accuracy and/or response time of radiation sensors employed for detection, and the speed of the implanted medical device. Improvement in one or more of these variables may compensate for one or more other variables. Optionally, reducing the speed of a tracked medical device may be employed to compensate for other variables. Optionally, location information is displayed in the context of anatomical imaging data. Optionally, relevant anatomical features are highlighted to facilitate navigation of the medical device by medical personnel. Optionally, determined positions may be displayed in the context of a separately acquired image.

Optionally, two or more sources may be tracked concurrently. Optionally, multi-source tracking is used in determining orientation of an asymmetric medical device. Optionally, multi-source tracking is used in coordinating activity of two or more medical devices for a medical procedure.

An aspect of some embodiments of the present invention relates to using a sensor with angular sensitivity (e.g., an angle-response sensor) to detect a direction towards a source of ionizing radiation. Optionally, two or three or more directions are determined, either concurrently or successively, so that a position may be determined by calculating an intersection of the directions. If three or more directions are employed, the location may be expressed as a three dimensional position. Optionally, a direction is used to determine a plane in which the source resides.

Optionally, sensors for detection of radiation from the source achieve the desired angular sensitivity by rotation of at least a portion of the sensor about an axis through a rotation angle. For example, detectors or radiation shields may be rotated. Alternately or additionally, sensors may achieve the desired angular sensitivity by translational motion.

An aspect of some embodiments of the present invention relates to a sensor with an angular sensitivity which causes changes in an output signal from at least one radiation detector in response to an effective angle of incidence between the detector and a source. A target value of the output signal is achieved at an angle indicating the direction towards the source. The direction is optionally used to determine a plane in which the source resides.

Optionally the sensor may include more than one radiation detector, each radiation detector having a separate output signal. Optionally, one or more radiation shields may be employed to shield or shadow at least a portion of at least one of the radiation detectors from incident radiation. The degree of shielding changes as deviation from the angle indicating a direction towards the source occurs and the output signal varies according to the degree of shielding.

Optionally, multiple radiation shields are employed in concert to form a collimator. The radiation shields may be either parallel to one another or skewed inwards. Optionally, the multiple radiation shield, whether parallel or skewed, may be rotated.

Optionally, the deviation from target output is 1% of the output range per milliradian of angular displacement away from an angle indicating a direction towards the source. Optionally deviation in output indicates direction of deviation as well as magnitude of deviation. According to various embodiments of the invention, radiation detectors and/or radiation shields may be displaced to impart angular sensitivity. This displacement may be rotational and/or translational.

In an exemplary embodiment of the invention, the sensor is designed to provide a useful angle dependent signal over a range of angles for a range of distances (e.g., a working volume). In an exemplary embodiment of the invention, the useful signal gives an accuracy of positioning of a source of better than 3 mm, better than 2 mm, better than 1 mm, or better, for example, 0.8 mm or better, when measured within one standard deviation. In an exemplary embodiment of the invention, the sensor includes a collimator. In an exemplary embodiment of the invention, this accuracy is an average accuracy over a tracking volume. Alternatively or additionally, the accuracy is a typical accuracy. Alternatively or additionally, the accuracy is a worst accuracy over the volume.

In an exemplary embodiment of the invention, the sensor and/or the collimator are designed so that different parts of the sensor have a different incidence angle to the source at which the signal is maximal (and/or minimal). Optionally, a composite signal from the sensor includes the contributions of multiple such parts.

In an exemplary embodiment of the invention, the sensor is designed for a particular working volume. The sensor includes at least two parts, one part having a maximum signal when aimed at a first target position relative to a center of said working volume and another part having a maximum signal when aimed at a second target position relative to a center of said working volume. Thus, the two parts cannot have a maximal signal at a same time. The angle of the sensor to the source is determined by a function of the signals from the two parts. Optionally, the sensor is designed with more than two maximal signal aiming targets, for example, three, four or more. In an exemplary embodiment of the invention, four such areas are used to provide both X and Y angular position indication using a single sensor.

In an exemplary embodiment of the invention, the sensor design trades-off an accuracy of angle/position determination achievable when the sensor is aimed at the target (e.g., at a location of maximum accuracy), with an accuracy for the working volume as a whole. Optionally, the two accuracies are about the same. Alternatively a ratio of between 1:4 and 4:1 is provided, for example, 1:2, 2:1 or intermediate values. Optionally, smaller or larger ratios are provided, for example depending on the application. In an exemplary embodiment of the invention, such ratios between accuracies are provided over a range of angles suitable for viewing a small translation, such as 5 mm, 10 mm, 20 mm or smaller, intermediate or larger values. Optionally, the translation is viewed at a distance of between 10 and 100 cm, for example, between 20 and 40 cm, or smaller or intermediate or larger distances.

In an exemplary embodiment of the invention, the sensor is used to track targets with a spatial layout of sources, optionally at different energies. Optionally, a sensor with a single or multiple aiming points generates different signals for different sources and the relative position of the sources is determined by the relative positions of the energy deposition on a suitable detector. Optionally, with a sensor having two aiming points, the peaks of the different sensor parts may be for different energies, reflecting the difference in relative spatial layout between the sources and the sensors. In one example, a catheter with two nearby sources at different energies is detected with the relative positions indicating the catheter (or other tool) orientation. It should be noted that in some embodiments of the invention, radiation from two nearby sources, can be detected simultaneously as both generate substantial counts on the sensor. This may be practiced with other sensors having a useful working volume.

An aspect of some embodiments of the present invention relates to a computerized system for locating a medical device, optionally within a body of a subject by using angular sensitivity of a sensor module to determine a direction. The sensor module measures incident radiation on one or more radiation detectors. Incident radiation produces an output signal which is translated to directional information by the system. Optionally, the directional information includes both direction and angle of offset from the direction. In an exemplary embodiment of the invention, the directional information is used to close a control loop. Optionally, the loop is designed so that the device or other source remains within a range of angles determinable by the sensor. Optionally, if the amount of angular motion of the device is smaller than the angular range of the sensors, the sensor is not moved and/or not rotated.

In an exemplary embodiment of the invention, the control loop includes rotation and/or translation of the sensor, so as to maintain the device and/or other source within a more accurate viewing/working volume of the sensor. Optionally, the maintaining takes into account a maximum expected motion of the device/source within a tracking period and/or an accuracy which can be achieved at angular/translational offsets caused by such motion.

In an exemplary embodiment of the invention, the control loop and/or sensor parameters are selected to take into account an expected device motion rate.

An aspect of some embodiments of the invention relates to at least partial optimization of a radioactive sensor system to take into account target motion of a radioactive source. In an exemplary embodiment of the invention, the optimization includes trading off an angular determination accuracy over a range of angles, with an absolute accuracy at a certain offset angle. Optionally, this results in a sensor with a useful working volume within which a useful (e.g., for the application) accuracy is achieved.

In an exemplary embodiment of the invention, the optimization allows sensor parameters to vary in a way which changes the optimal aiming of different parts of the sensor array.

In an exemplary embodiment of the invention, one or more of the following parameters of a collimator of the sensor are varied during optimization: slant geometry, aiming point location and/or aiming point shape.

In an exemplary embodiment of the invention, one or more of the following are provided as part of a cost function for the optimization: depth of field, motion speed, static accuracy, dynamic accuracy and/or patient motion parameters.

In an exemplary embodiment of the invention, optimization is optimization of a collimator design for a given sensor and usage conditions. Optionally, the optimization includes a simulation of signals expected to be detected and, optionally, expected noise sources.

Optionally, optimization comprises selecting a best collimator from a set of collimators, for example a set including between 3 and 20 collimators, for example, between 4 and 10 collimators, for example, 5 or 9 collimators. Larger, smaller and intermediate numbers of collimators may be provided in a set.

In an exemplary embodiment of the invention, a collimator comprises a frame including one or more slotted plates, each of which plates align slats relative to a detector element. Optionally, the frame is adapted for mounting the detector thereon. Optionally, the slotted plates are replaceable. Optionally, one or more screws and/or motors are provided for moving, adjusting and/or calibrating the relative slat angles. Optionally, a motor is provided to rotate the frame as a whole.

An aspect of some embodiments of the invention relates to association of a source of ionizing radiation with a medical device to facilitate determination of a location of the device, optionally as the device is navigated within or near a subject's body during a medical procedure. Optionally, the source of ionizing radiation has an activity in the range of 0.01 mCi to 0.5 mCi. Optionally, the source of ionizing radiation has an activity less than 0.1 mCi. Optionally, the source of ionizing radiation has an activity of about 0.05 mCi. Association includes integrally forming the source and the device as a single unit. Association also includes attaching the source to the device. Optionally, the source is concentrated in an area having a largest dimension less than 10 mm, optionally less than 5 mm, optionally less than 2.5 mm, optionally less than 1 mm.

An aspect of some embodiments of the invention relates to use of an ionizing radiation source with an activity of 0.1 mCi or less as a target for non imaging localization or tracking, optionally in a medical context. The source of ionizing radiation is selected to reduce a biological effect on the patient and/or medical personnel. This selection involves consideration of radiation strength, radiation type and/or amount of exposure time (e.g. time in the body for a patient undergoing a procedure). Alternatively or additionally, radiation sources which are constructed of biocompatible material and/or coated with biocompatible coatings may be employed.

In an exemplary embodiment of the invention, a computerized system for tracking and locating a source of ionizing radiation is provided. The system comprising:

(a) at least one non-imaging sensor module comprising at least one radiation detector, the at least one radiation detector capable of receiving ionizing radiation from the radiation source and producing an output signal; and (b) the CPU designed and configured to receive the output signal and translate the output signal to directional information.

Optionally, the source of radiation is integrally formed with or attached to a medical device.

Optionally, the at least one sensor module includes at least two sensor modules.

Optionally, the at least two sensor modules includes at least three sensor modules.

Optionally, the at least one of the at least one sensor module further comprises a locomotion device capable of imparting translational or rotational motion to the sensor module so that the sensor module is moved to a new location.

Optionally, the locomotion device is operable by a translational or rotational motion signal from the CPU.

Optionally, the system additionally comprises an imaging module, the imaging module capable of providing an image signal to the CPU, the CPU capable of translating the image signal to an image of a portion of the body of the subject.

Optionally, the system further comprises a display device.

Optionally, the display device is capable of displaying the image of the portion of the body of the subject with a determined position of the medical device superimposed on the image of the portion of the body of the subject.

Optionally, the CPU receives at least two of the output signals and computes a position of the radiation source based on the output signals.

Optionally, the CPU receives at least three of the output signals and computes a position of the radiation source based on the at least three output signals.

Optionally, the CPU computes the position repeatedly at intervals so that a position of the radiation source as a function of time may be plotted.

Optionally, the radiation source employs an isotope with a half life in the range of 6 to 18 months.

Optionally, the system further comprises the radiation source capable of providing the radiation.

Optionally, the directional information is produced when the source has an activity in the range of 0.01 mCi to 0.5 mCi.

In an exemplary embodiment of the invention, a sensor for directionally locating an ionizing radiation source is provided. The sensor comprises:

(a) at least one functional component; and (b) a displacement mechanism which imparts angular sensitivity to the sensor by moving the at least one functional component.

Optionally, the at least one functional component comprises at least one radiation detector, the at least one radiation detector capable of receiving radiation from the radiation source and producing an output signal;

wherein the displacement mechanism is capable of rotating the at least one radiation detector through a rotation angle so that the output signal varies with the rotation angle.

Optionally, the at least one radiation detector comprises at least one first radiation detector and at least one second radiation detector and the output signal comprises at least one first output signal from the at least one first radiation detector and at least one second output signal from the at least one second radiation detector.

Optionally, the sensor comprises at least one radiation shield installed at a fixed angle with respect to the at least one first radiation detector and the at least one second radiation detector so that a magnitude of the first output signal from the at least one first radiation detector and a magnitude of the second output signal from the second radiation detector vary with the rotation angle.

Optionally, the sensor comprises:

(a) at least one first radiation detector and at least one second radiation detector, each of the at least one first radiation detector and at least one second radiation detector capable of receiving radiation from the radiation source and producing at least one first output signal from the at least one first radiation detector and at least one second output signal from the at least one second radiation detector;

(b) at least one radiation shield, the radiation shield rotatable about an axis of shield rotation through an angle of shield rotation, so that a magnitude of the first output signal from the at least one first radiation detector and a magnitude of the second output signal from the second radiation detector each vary with the angle of shield rotation.

Optionally, the at least one radiation shield comprises:

(i) a primary radiation shield located between the at least one first radiation detector and the at least one second radiation detector;

(ii) at least one first additional radiation shield deployed to interfere with incident radiation directed towards the at least one first radiation detector; and (iii) at least one second additional radiation shield deployed to interfere with incident radiation directed towards the at least one second radiation detector.

Optionally, wherein the at least one first additional radiation shield and the at least one second additional radiation shield are each inclined towards the primary radiation shield.

Optionally, wherein the at least one first radiation detector and the at least one second radiation detector are organized in pairs, each pair having a first member and a second member and each radiation shield of the primary and additional radiation shields is located between one of the first member and one of the second member of one of the pairs so that the output signal varies with the rotation angle.

Optionally, the sensor is additionally capable of revolving the at least a functional component about an axis of revolution through an angle of revolution.

In an exemplary embodiment of the invention, a method of determining a location of a device is provided. The method comprises:

(a) providing a device having a radiation source associated therewith;

(b) determining a direction towards the radiation source;

(c) further determining at least a second direction towards the radiation source;

(d) locate the device by calculating an intersection of the first direction and the at least a second direction.

Optionally, the further determining at least a second direction towards the radiation source includes determining at least a third direction towards the radiation source and additionally comprising:

(e) calculating a point of intersection of the first direction, the second direction and the at least a third direction.

In an exemplary embodiment of the invention, a method of manufacturing a trackable medical device is provided. The method comprises incorporating into or fixedly attaching a detectable amount of a radioactive isotope to the medical device.

Optionally, the detectable amount is in the range of 0.01 mCi to 0.5 mCi.

Optionally, the detectable amount is 0.1 mCi or less.

Optionally, the detectable amount is 0.05 mCi or less.

Optionally, the isotope is Iridium-192.

An aspect of some embodiments of the invention relates to use of an ionizing radiation source with an activity of 0.1 mCi or less as a target for non imaging localization or tracking.

There is also provided in accordance with an exemplary embodiment of the invention, an angle-responsive sensor, comprising:

a radiation detector adapted to detect ionizing radiation;

at least one radiation absorbing element arranged to block radiation from reaching said detector in a manner dependent on a relative orientation of a radiation source, said detector and said element, said detector and said element defining an aim for said sensor; and circuitry coupled to said detector and which generates an output signal which varies as a function of said relative orientation, wherein said detector and said element are arranged to have a working volume of at least 10 cm in depth and having an angular width, such that said signal defines an accuracy of better than 3 mm within one standard deviation, over said working volume.

Optionally, said accuracy is better than 2 mm. Optionally, said accuracy is better than 1 mm.

In an exemplary embodiment of the invention, said signal is near linear over said working volume.

In an exemplary embodiment of the invention, a ratio between an accuracy when said sensor is aimed at said source and when said sensor is at an angle within said working volume, is between 1:4 and 4:1.

In an exemplary embodiment of the invention, said working volume has an angular range of at least 10 milliradians.

In an exemplary embodiment of the invention, said working volume has an angular range of at least 20 milliradians.

In an exemplary embodiment of the invention, said circuitry generates said signal based on a combining of contributions of at least two separate sections of said detector. Optionally, said two sections each have different angular direction of maximum detection.

In an exemplary embodiment of the invention, the sensor comprises a motor configured to rotate said sensor and change its aim thereby.

In an exemplary embodiment of the invention, said circuitry generates said signal for a source distance of at least 10 cm.

In an exemplary embodiment of the invention, said circuitry generates said signal for a source distance of at least 20 cm.

In an exemplary embodiment of the invention, said working volume has a range of depths having a ratio of at least 1:2.

There is also provided in accordance with an exemplary embodiment of the invention, a multi-focal non-imaging radiation sensor, comprising:

a detector comprising at least two distinguishable sections; and a collimator arranged to differently collimate radiation on each of said sections. Optionally, the sensor comprises two sections, each one with a different focal area. Alternatively or additionally, said collimator provides multiple focal points for each of said sections.

In an exemplary embodiment of the invention, said collimator allows wide angle radiation at a spatial angle of at least 10 degrees for at least two sections.

In an exemplary embodiment of the invention, a focal point of a first section is distanced from a focal point of a second section in a direction parallel to said detector, a distance of at least 1 mm. Optionally, the sensor comprises additional sections with additional focal points distanced along said parallel direction. Alternatively or additionally, said sensor has a relatively linear angular response over an angle range of at least 10 milliradians. Alternatively or additionally, said sensor has a relatively linear angular response over a depth range of at least 10 cm.

There is also provided in accordance with an exemplary embodiment of the invention, a method of collimator design, comprising:

defining an object range and movement rate; and determining a collimator design responsive to said defining which has a linear-like angular response within said range and suitable for tracking said movement rate. Optionally, the method comprises generating a collimator according to said determining. Alternatively or additionally, the method comprises selecting a collimator according to said determining.

In an exemplary embodiment of the invention, determining comprises optimizing.

In an exemplary embodiment of the invention, determining comprises determining in response to a desired accuracy of said angular response.

There is also provided in accordance with an exemplary embodiment of the invention, a method of collimator design, comprising:

defining an object range, movement rate and accuracy; and determining a collimator design responsive to said defining which has said accuracy over said range and suitable for tracking said movement rate.

There is also provided in accordance with an exemplary embodiment of the invention, a collimator set, comprising:

at least two collimators, each collimator having a better angular-accuracy under a different set of conditions, each set of conditions defining a depth and an angular range, said two sets differing in at least one of depth and angular range, said angular ranges being greater than 10 milliradians.

In an exemplary embodiment of the invention, the set includes collimators for at least three different angular ranges.

In an exemplary embodiment of the invention, the set includes collimators for at least three different depths.

There is also provided in accordance with an exemplary embodiment of the invention, a method of tracking a radioactive object, comprising:

(a) aiming at least one non-imaging sensor at said object;

(b) detecting an angular offset of said object from said sensor, based on a radiation detection by said sensor;

(c) re-aiming said sensor at said object according to said angular offset by automatic circuitry; and (d) repeating (b)-(c) at least 10 times within a minute.

Optionally, said re-aiming does not aim said sensor exactly at said target at least 50% of the time.

In an exemplary embodiment of the invention, said re-aiming comprises an estimate of a current position of the object.

In an exemplary embodiment of the invention, said re-aiming comprises an estimate of a future position of the object.

BRIEF DESCRIPTION OF FIGURES

In the Figures, identical structures, elements or parts that appear in more than one Figure are generally labeled with the same numeral in all the Figures in which they appear. Dimensions of components and features shown in the Figures are chosen for convenience and clarity of presentation and are not necessarily shown to scale. The Figures are listed below.

DETAILED DESCRIPTION OF EMBODIMENTS

According to one embodiment of the invention (FIGS. 2 and 4), a computerized system 40 locates and/or tracks a device. In the embodiment depicted in FIG. 4, the device is a medical device. Medical devices include, but are not limited to, tools, implants, navigational instruments and ducts. Tools include, but are not limited to, catheters, canulae, trocar, cutting implements, grasping implements and positioning implements. Implants include, but are not limited to, brachytherapy seeds, stents and sustained release medication packets. Navigational instruments include, but are not limited to, guidewires. Ducts include, but are not limited to, tubing (e.g. esophageal tubes and tracheal tubes). In exemplary embodiments of the invention, one or more moving tools are tracked.

In an exemplary embodiment of the invention, position of the source is determined by non-imaging data acquisition. For purposes of this specification and the accompanying claims, the phrase "non-imaging" indicates data not acquired as part of an image acquisition process that includes the source and anatomical or other non-source features in a same image. Optionally, a sensor which is not suitable for and not connected to imaging circuitry is employed. Imaging relies upon information about many points, including at least one point of interest, and image analysis of the information determines characteristics of the point(s) of interest, for example position relative to an object. In an exemplary embodiment of the invention, position sensing provides information only about the source. This can improve detectability and/or accuracy.

Figure 4:
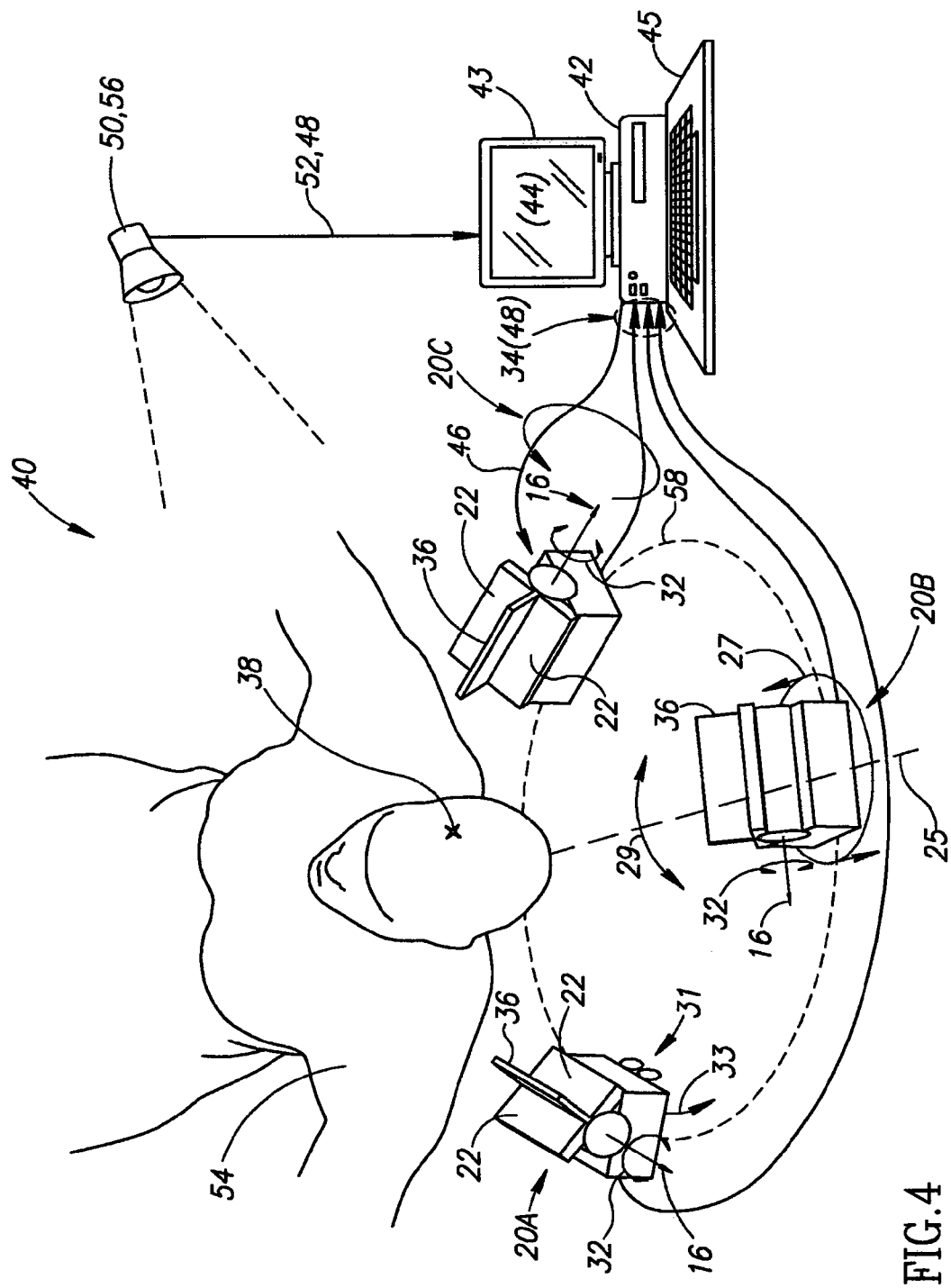
FIG. 4 is a perspective view of a computerized tracking system according to an exemplary embodiment of the present invention illustrating one possible arrangement of sensor modules with respect to a patient.

Optionally, the medical device is at least partially within a body of a subject 54 during at least part of the path upon which its location is determined. In FIG. 4, an exemplary embodiment in which system 40 is configured to track a device through the head of subject 54 during an intracranial medical procedure is depicted. This drawing is purely illustrative and should not be construed as a limitation of the scope of the invention.

Figure 1:
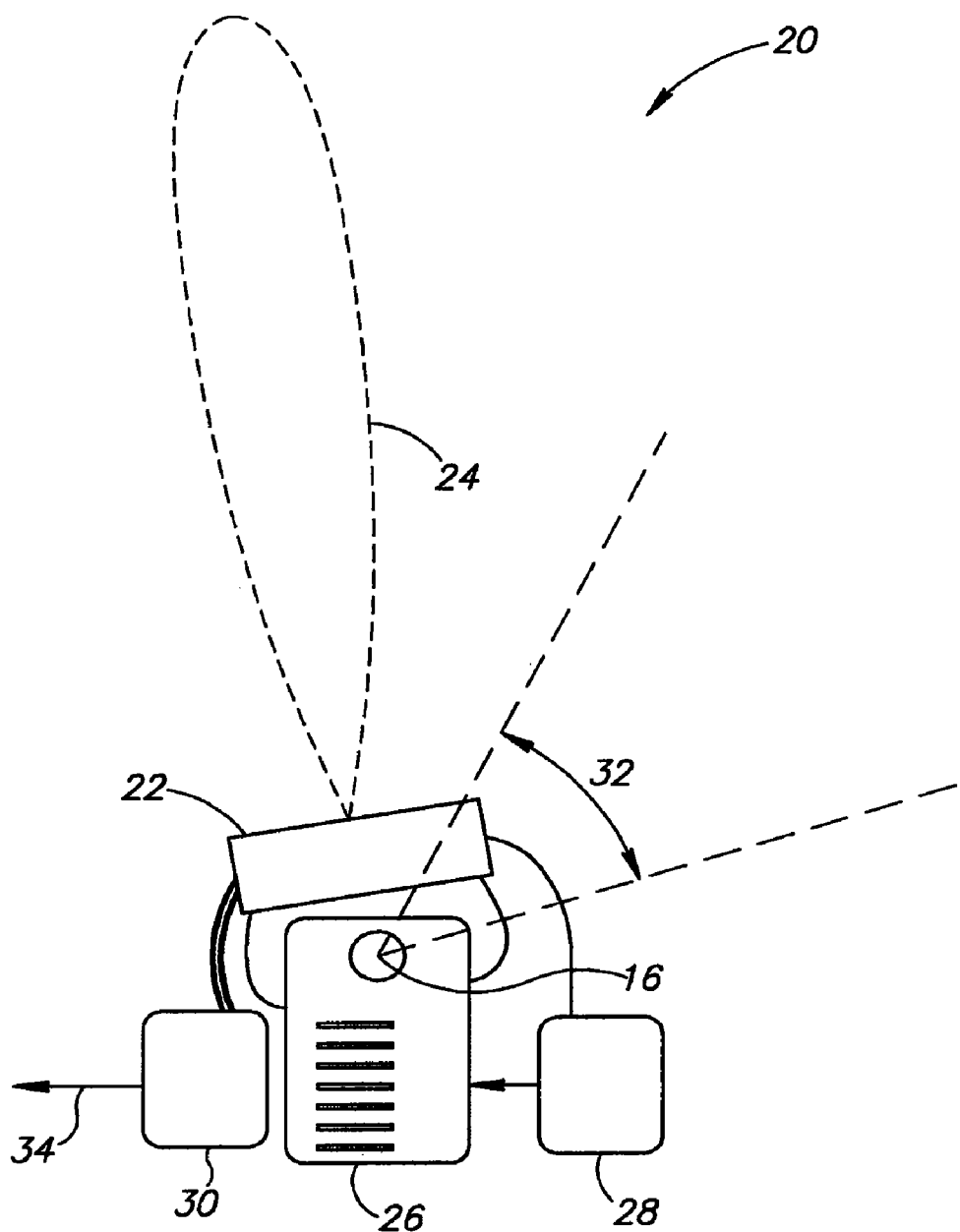
FIG. 1 is a side view of one embodiment of a sensor module according to an exemplary embodiment of the present invention.
Figure 2:
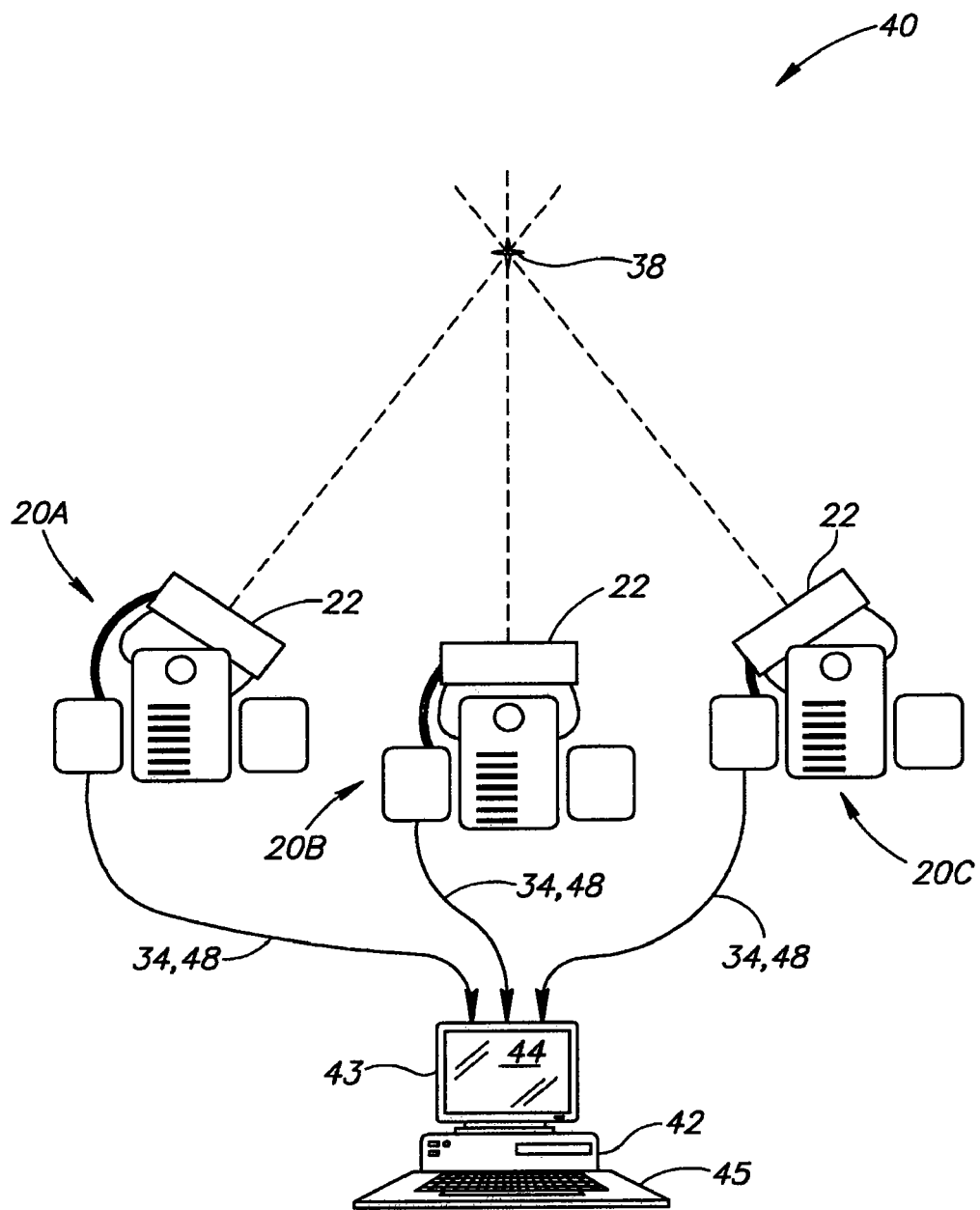
FIG. 2 is a schematic representation of a computerized tracking system according to an exemplary embodiment of the present invention.

FIG. 2 shows an embodiment of system 40 including three sensor modules 20 which rely on angular detection acting in concert to determine a location of radioactive source 38. In the pictured embodiment, each of sensors 20 determines an angle of rotation 32 indicating a direction towards source 38. This angle of rotation 32 (FIG. 1) defines a plane in which source 38 resides and which crosses radiation detector 22. Angle of rotation 32 is provided as an output signal 34 which is relayed to computerized processing unit (CPU) 42. CPU 42 determines an intersection of the three directions (planes) which is expressed as a point. FIG. 1 also shows a rotation axis 16 around which detector 22 is rotated in some embodiments of the inventions.

According to some embodiments of the invention, a source 38 located within the boundaries 24 of detection (FIG. 1) of sensor 20 may be accurately located by system 40 as radiation detector 22 of sensor module 20 is rotated through a series of rotation angles 32. A source 38 located outside of boundaries 24 will not be accurately located. For this reason, it is desirable, in some embodiments, that each of sensors 20 is deployed so that the predicted path of source 38 lies within boundaries 24. According to some embodiments of the invention, sensor 20 may move to keep source 38 within boundaries 24. The size and shape of boundaries 24 vary according to the configuration of sensor 20.

Accuracy of determination of target rotation angle 32 contributes to accuracy of the location of source 38 as determined by system 40. Various modifications to sensor module 20 which can increase the sensitivity to small differences in rotation angle 32 are depicted as exemplary embodiments in FIGS. 3, 5, 6A and 6B and explained in greater detail hereinbelow.

FIG. 4 provides a perspective view of an exemplary system 40 which employs angular detection and includes three sensor modules 20 dispersed upon the circumference of a circle 58. In the pictured embodiment, modules 20 feature radiation shields 36. In the pictured embodiment, each module 20 rotates about an axis tangent to circle 58. This rotation allows tracking of the medical device as explained in greater detail hereinbelow. According to various embodiments of the invention, rotational motion or translational motion may be employed to facilitate the desired angular detection. According to the embodiment depicted in FIG. 4, sensor modules 20 are situated below the head of subject 54 such that the vertical distance between the plane of sensor modules 20 and the region of interest within the head is approximately equal to the radius of circle 58. This arrangement assures that each of sensors 20 are deployed so that the predicted path of source 38 lies within boundaries 24. This arrangement may be repeatably and easily achieved by providing three of sensors 20 mounted on a board equipped with a raised headrest in the center of circle 58. This optionally permits a reclining chair or adjustable examination table to be easily positioned so that subject 54 is correctly placed relative to sensors 20 without an extensive measuring procedure.

Other arrangements of the sensors can be provided as well, for example, the sensor modules 20 can be configured in any geometric configuration in which the intersection of the planes containing their respective rotation axes and source 38 provides observability of the 3D location of source 38.

Figure 19:
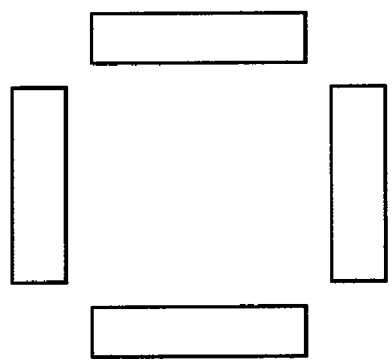
FIGS. 19-21 illustrate exemplary detector configurations in accordance with exemplary embodiments of the invention.
Figure 20:
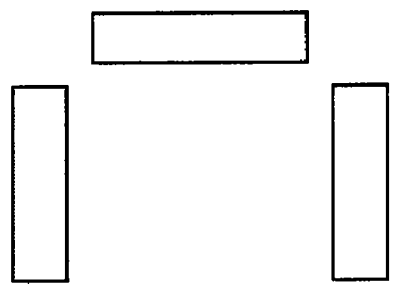
Figure 21:
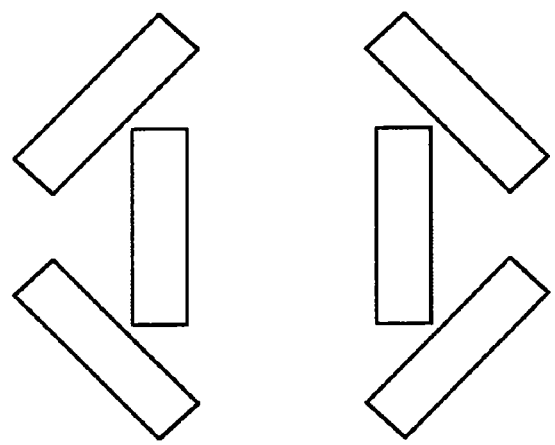

In particular, FIGS. 19-21 show three exemplary alternative configurations, where each rectangle represents a single sensor. FIG. 19 shows a square arrangement. FIG. 20 shows an open square, absent one of the sensors of FIG. 19, which may be suitable if access to patient is desired from the open side. For example, the arrangement may be 50 cm in diameter. In an exemplary embodiment of the invention, the arrangement is mounted on an arm (e.g., a gooseneck-type arm) and is positioned by a user to be, for example, near a breast (for tracking radiation therein, for example for guiding a biopsy needle). FIG. 19 is also suitable for mounting on a movable/adjustable arm.

FIG. 21 shows an embodiment where the spacing between sensors in a diamond arrangement was increased, for example, to allow passage of a therapeutic beam or a tool. Additional sensors bracketing the spacing are provided.

It should be appreciated that three sensors are generally enough for position determining. In an exemplary embodiment of the invention, additional sensors are provided so that a more accurate estimation of position is made, for example, by selecting a center of gravity of positions determined by sets of three sensors. Alternatively or additionally, the use of more than three sensors provides an estimation of error, for example, based on the distance between the extreme possible positions reconstructed from measurements. Alternatively or additionally, multiple sensors are provided to enhance accuracy in some parts of a positioning volume (described below as a reference 40), or to increase such a volume.

It should also be appreciated that the sensor shape need not be a rectangle, for example, a circle, square or other shapes may be used in some embodiment. In particular, a circle can be rotated around two axes to provide a line in space, rather than a plane. This may be useful for guiding a biopsy needle or a therapeutic beam or an illumination beam along this line in space towards a radioactive source in a patient.

Positioning volume of system 40 is the set of spatial coordinates in which a location of source 38 may be determined. Positioning volume of system 40 has a size and/or shape dependent upon positions of sensor(s) 20, their design and/or their performance characteristics. Optionally, positioning volume of system 40 can be expressed as the intersection of boundaries of detection 24 of sensors 20. Optionally, two or more positioning volumes may be created, by using multiple sets of sensors 20. Optionally, these positioning volumes may overlap.

The 3-dimensional position of the center of mass of a radiation source 38 is calculated by CPU 42 from the angle 32 measured by each of sensor modules 20, given the known location and rotation axis of each of modules 20. According to some embodiments of the invention, source 38 will be a piece of wire with a length of 1 to 10 mm. This range of lengths reflects currently available solid isotope sources 38 supplied as wires with useful diameters and capable of providing a sufficient number of DPM to allow efficient operation of system 40. System 40 determines the position of the middle of this piece of wire 38 and resolves the determined position to a single point, optionally indicating margins of error.

Sensor module 20 includes at least one radiation detector 22. Radiation detector 22 is capable of receiving radiation from radiation source 38 attached to the medical device and producing an output signal 34. Radiation detector 22 may employ any technology which transforms incident radiation into a signal which can be relayed to CPU 42. If source 38 is a gamma radiation source, radiation detector 22 may be, for example, an ionization chamber, a Geiger-Mueller Counter, a scintillation detector, a semiconductor diode detector, a proportion counter or a micro channel plate based detector. Radiation detectors 22 of various types are commercially available from, for example, EVproducts (Saxonburg Pa., USA); Hammatsu Photonics (Hamamatsu City, Shizuoaka, Japan); Constellation Technology, (Largo, Fla., USA); Soltec Corporation (San Fernando Calif., USA); Thermo Electron Corporation, (Waltham Mass., USA); Bruker-biosciences (Billerica Mass., USA); Saint Gobain crystals (Newbury Ohio, USA) and Silicon Sensor GMBH (Germany). A suitable commercially available radiation detector 22 can be incorporated into the context of system 40 as part of sensor 20. Embodiments of the invention which rely upon a source 38 producing a small number of DPM and types of detectors 22 which offer good sensitivity (i.e. high ratio between CPM and DPM) will improve the performance of sensor modules 20. As the distance between sensor 20 and source 38 increases, this consideration becomes more relevant. Embodiments of the invention which rely upon source 38 with a greater DPM output may permit use of less sensitive radiation detectors 22.

Various types of sensor modules 20 are described in greater detail hereinbelow.

System 40 further includes radiation source 38 capable of providing a sufficient amount of radiation for location and/or tracking at a rate which will not adversely affect a procedure being carried out by the medical device. For most medical procedures, 10 locations/second is sufficient to allow an operator of system 40 to comfortably navigate the medical device to a desired location. Based upon results from a computerized simulation described in greater detail hereinbelow, the amount of radiation to meet these criteria can be made low enough that it does not pose any significant risk to a patient undergoing a procedure of several hours duration with source 38 inside their body. Alternatively or additionally, the amount may be made low enough so that an operator of system 40 is not exposed to any significant risk from radiation exposure over time as explained hereinbelow.

Figure 9A:
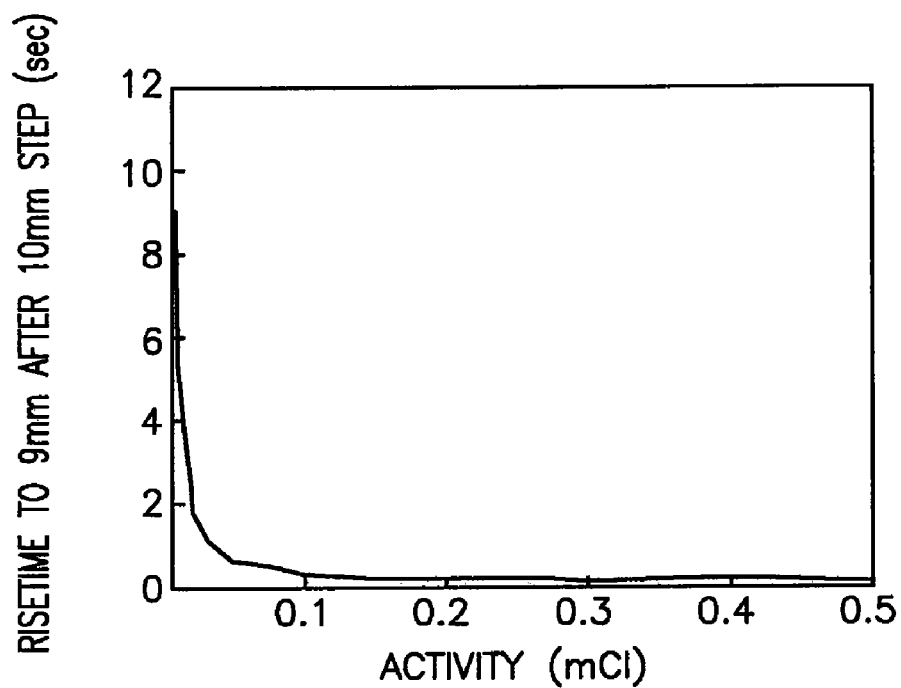
FIGS. 9A and 9B are graphs of simulated response time and simulated rms position error respectively plotted as a function of specific activity of a radioactive signal source using a system according to an exemplary embodiment of the present invention.
Figure 9B:
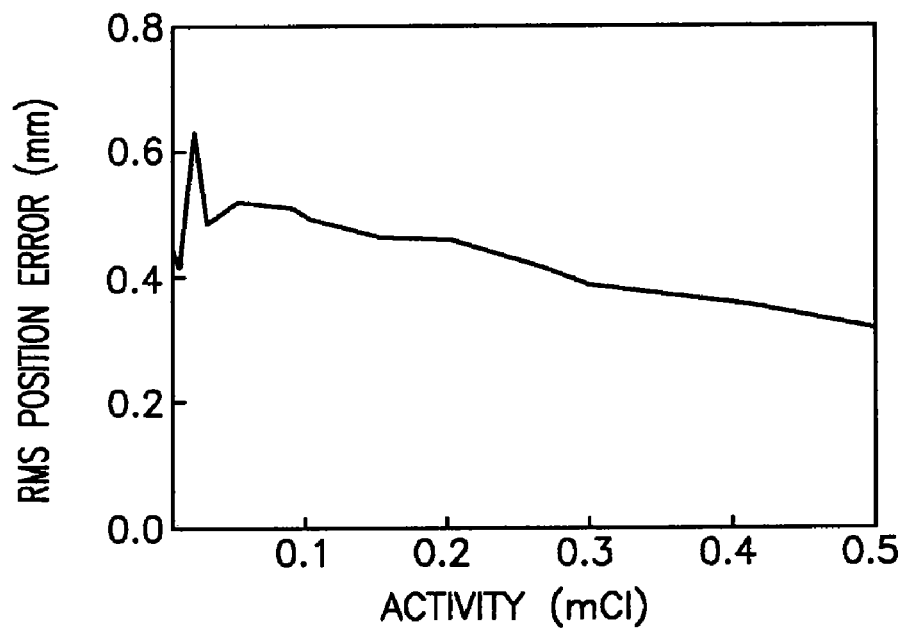

For example, using Iridium-192 increasing the activity of radiation source 38 from 0.01 mCi to 0.5 mCi improves accuracy only by a factor of 2 (FIG. 9B). However, activity levels below 0.1 mCi adversely affect response time (FIG. 9A). Activities greater than 0.1 mCi do not significantly improve response time. An activity of 0.05 mCi offers an acceptable trade-off between latency and accuracy as described in greater detail hereinbelow and provides a good compromise between performance and radiation dose.

A 0.05 mCi source 38 permits system 40 to achieve adequate speed and accuracy with an amount of radiation produced so low that it may be safely handled without gloves. Radiation exposure for the patient from a 0.05 mCi source 38 is only eight times greater than average absorbed background radiation in the United States. For purposes of comparison to previously available alternatives, a 0.05 mCi source 38 exposes the patient to an Effective Dose Equivalent (EDE) of 0.0022 mSv/hr. A typical fluoroscopy guided procedure has an EDE of 1-35 mSV per procedure and a typical Nuclear Medicine procedure has an EDE of 5 mSv. Thus, some embodiments of the invention may be employed to significantly reduce patient radiation exposure.

Medical personnel are optionally exposed to even less radiation, with the level of exposure decreasing in proportion to the square of the intervening distance. For example, a doctor located one meter from a 0.05 mCi source 38 and performing procedures for 6 hours per day, 5 days a week, 52 weeks a year would accumulate a total annual EDE of 0.22 mSv. This is approximately 5% of the radiation exposure level at which exposure monitoring is generally implemented. This level of exposure corresponds to $1.4e^{-4}$ mSV/hr which is orders of magnitude less than the 1-12 mSv/hr associated with a typical dose from fluoroscopic procedures.

Iridium-192 has been used as an example because it is already approved for use in medical applications and is generally considered safe to introduce into the body of a subject. However, this isotope is only an illustrative example of a suitable source 38, and should not be construed as a limitation of system 40. When choosing an isotope for use in the context of system 40, activity (DPM), type of radiation and/or half life may be considered. Activity has been discussed above. In addition, it is generally desired that disintegration events be detectable with reasonable efficiency at the relevant distance, for example 20-50 cm. Long half lives may be preferred because they make inventory control easier and reduce total costs in the long run by reducing waste. However, short half lives may reduce concerns over radioactive materials and/or may allow smaller sources to be used.

According to some embodiments of the invention, source 38 is a source of positron emissions. According to these embodiments, sensors 20 determine a direction from which photons released as a result of positron/electron collisions originate. This difference optionally does not affect accuracy of a determined location to any significant degree because the distance traveled by a positron away from source 38 before it meets an electron is generally very small. Use of positrons in source 38 can effectively amplify total ionizing radiation emissions available for detection. Optionally, the use of multiple detector may allow the detection of pairs of positron annihilation events to be detected. Other examples of source types include gamma sources, alpha sources, electron sources and neutron sources.

Regardless of the isotope, source 38 may be incorporated into a medical device (e.g. guidewire or catheter) which is to be tracked. Incorporation may be, for example, at or near the guidewire tip and/or at a different location in a catheter or in an implant. The source of ionizing radiation may be integrally formed with, or attached to, a portion of the guidewire or to a portion of the medical device. Attachment may be achieved, for example by gluing, welding or insertion of the source into a dedicated receptacle on the device. Attachment may also be achieved by supplying the source as an adhesive tag (e.g. a crack and peel sticker), paint or glue applicable to the medical device. Optionally, the source of ionizing radiation is supplied as a solid, for example a length of wire including a radioactive isotope. A short piece of wire containing the desired isotope may be affixed to the guidewire or medical device. This results in co-localization of the medical device and the source of radiation. Affixation may be accomplished, for example, by co-extruding the solid source with the guidewire during the manufacture of the guide wire. Alternately, or additionally, the source of ionizing radiation may be supplied as a radioactive paint which can be applied to the medical device and/or the guidewire. Regardless of the exact form in which the ionizing radiation source is supplied, or affixed to the guidewire or medical device, it should not leave any significant radioactive residue in the body of the subject after removal from the body at the end of a medical procedure.

While source 38 is illustrated as a single item for clarity, two or more sources 38 may be tracked concurrently by system 40. System 40 may identify multiple sources 38 by a variety of means including, but not limited to, discrete position or path, frequency of radiation, energy of radiation or type of radiation. According to some embodiments of the invention, use of two or more resolvable sources 38 provides orientation information about the item being tracked. In other words, these embodiments permit determination of not only a 3-dimensional position defined by co-ordinates X, Y and Z, but also information about the orientation of the tracked object at the defined location. This feature is relevant in a medical context when a non-symmetrical tool is employed.

System 40 may include a channel of communication 48 capable of conveying a data signal between the one or more sensor modules 20 and a computerized processing unit (CPU) 42. Channel of communication may be wired or wireless or a combination thereof. Wired channels of communication include, but are not limited to, direct cable connection, telephone connection via public switched telephone network (PSTN), fiber optic connection and construction of system 40 as an integrated physical unit with no externally apparent wires. Wireless channels of communication include, but are not limited to infrared transmission, radio frequency transmission, cellular telephone transmission and satellite mediated communication. The exact nature of channel of communication 48 is not central to operation of system 40 so long as signal transmission permits the desired refresh rate. Channels of communication 48 may optionally permit system 40 to be operated in the context of telemedicine. Alternately, or additionally, channels of communication 48 may serve to increase the distance between source 38 and medical personnel as a means of reducing radiation exposure to the medical personnel to a desired degree.

CPU 42 is designed and configured to receive output signal 34 via channel of communication 48 and translate output signal 34 to directional information concerning radiation source 38. This directional information may be expressed as, for example, a plane in which radiation source 38 resides. Output signal 34 includes at least rotation angle 32. Optionally, output signal 34 may also include a signal strength indicating component indicating receipt of a signal from source 38. Receipt of a signal from source 38 may be indicated as either a binary signal (yes/no) or a signal magnitude (e.g. counts per minute). According to various embodiments of the invention, output signal 34 may be either digital or analog. Translation of an analog signal to a digital signal may be performed either by sensor module 20 or CPU 42. In some cases, locating radiation source 38 in a single plane is sufficient. However, in most embodiments of the invention, it is desirable that CPU 42 receives two of output signals 34 and computes an intersection. If output signals 34 are expressed as planes, this produces a linear intersection 44 of two of the planes. This locates radiation source 38 upon the linear intersection 44. Optionally, results 44 of this calculation are displayed on a display device 43 as described in greater detail hereinbelow. In additional embodiments of the invention, CPU 42 receives at least three of output signals 34 and computes their intersection. If output signals 34 are expressed as planes and sensors 20 are positioned on the circumference of circle 58, this produces a point of intersection 44 of at least three planes, thereby locating radiation source 38 at the calculated point of intersection 44.

Figure 10A:
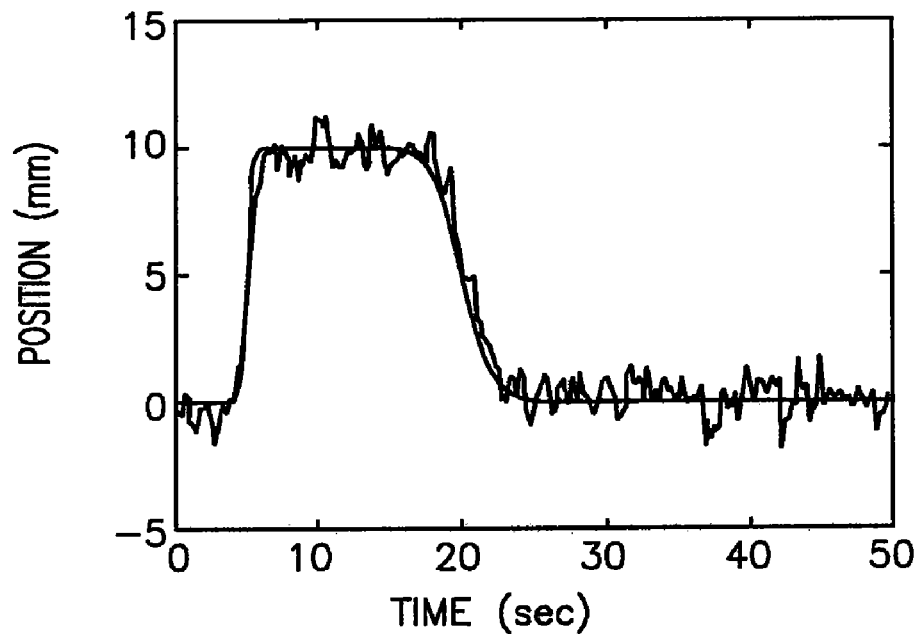
FIG. 10A is a graph of position as a function of time. Simulated position output from a system according to an exemplary embodiment of the present invention is overlaid on a plot of actual input position for the simulation.
Figure 10B:
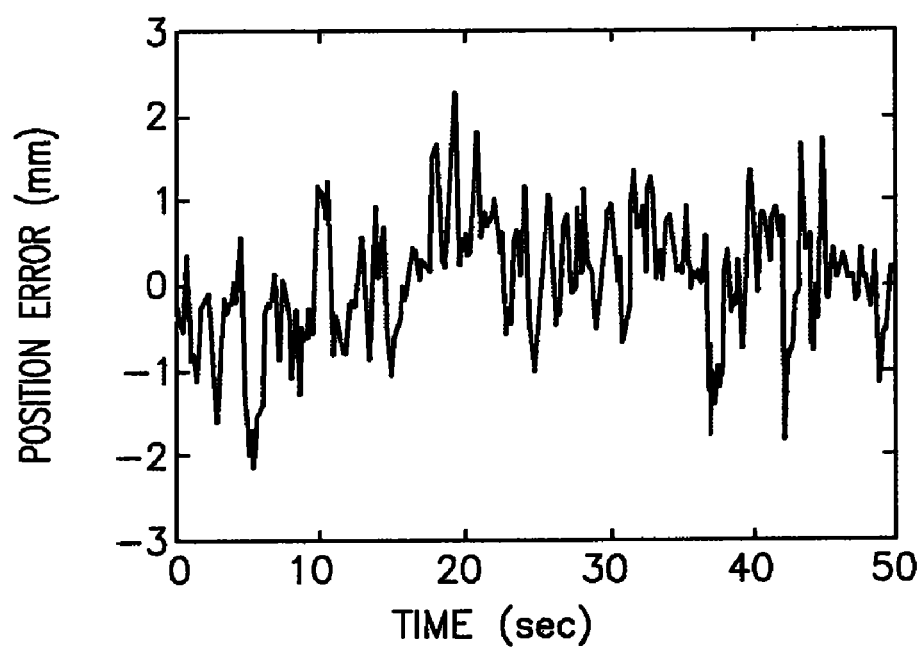
FIG. 10B is a graph of rims position error plotted as a function of time based upon the two plots of FIG. 10A.

Because system 40 is most often employed to track a medical instrument during a medical procedure, CPU 42 is often employed to compute the point of intersection repeatedly at predetermined intervals so that a position of radiation source 38 as a function of time may be plotted (see FIG. 10A). The accuracy of each plotted position and of the plot as a whole may be influenced by the activity of source 38, the accuracy and response time of sensors 20 and the speed at which the implanted medical device is moving through subject 54. Because medical procedures generally favor precision over speed, an operator of system 40 may compensate for deficiencies in source 38, or accuracy or response time of sensors 20, by reducing the rate of travel of the medical device being employed for the procedure. FIG. 10B illustrates output of a simulated system 40 with tracking accuracy in the range of ±2 mm. CPU 42 may also optionally employ channel of communication 48 to send various signals to sensor module(s) 20 as detailed hereinbelow. Alternately, or additionally, CPU 42 may also optionally employ channel of communication 48 to send various signals to the medical device. According to various embodiments of the invention, system 40 may be employed in the context of procedures including, but not limited to, angioplasty (e.g. balloon angioplasty), deployment procedures (e.g. stent placement or implantation of radioactive seeds for brachytherapy), biopsy procedures, excision procedures and ablation procedures.

While CPU 42 is depicted as a single physical unit, a greater number of physically distinct CPUs might actually be employed in some embodiments of the invention. For example, some functions, or portions of functions, ascribed to CPU 42 might be performed by processors installed in sensor modules 20. For purposes of this specification and the accompanying claims, a plurality of processors acting in concert to locate source 38 as described herein should be viewed collectively as CPU 42.

According to some embodiments of the invention, system 40 concurrently employs three or more sensor modules 20 in order to concurrently receive three or more output signals 34 and compute three or more directions indicating signal source 38. If the directions are expressed as planes, the three or more planes intersect in a single point. However, system 40 includes alternate embodiments which employ two, or even one, sensor module 20 to localize source 38 to a single point. This may be achieved in several different ways as described hereinbelow.

According to some embodiments of system 40 at least one of sensor module 20 is capable of rotating the at least one radiation detector 22 through a series of positions. Each position is defined by a rotation angle 32 so that receiving the radiation from source 38 upon detector 22 varies with rotation angle 32. This rotation may be accomplished in a variety of ways. For example, rotation mechanism 26 may be operated by feedback from 28 from radiation detector 22 according to a rule with amount of received radiation as a variable. Alternately, rotation mechanism 26 may be operated by a signal from CPU 42 according to a rule including amount of received radiation and/or time as variables. Alternately, rotation mechanism 26 may rotate radiation detector 22 according to a fixed schedule, with no regard to how much radiation impinges upon radiation detector 22 at any particular rotation angle 32. Rotation mechanism 26 may employ a wide variety of different mechanisms for achieving rotation angle 32. These mechanisms include, but are not limited to, mechanical mechanisms, hydraulic mechanisms, pneumatic mechanisms, electric mechanisms, electronic mechanisms and piezoelectric mechanisms. Optionally, an independent angle measuring element 30 may be employed to more accurately ascertain the actual rotation angle 32. Although angle measuring element 30 is depicted as a physically distinct component in FIGS. 1, 2 and 3, it could be physically integrated into rotation mechanism 26 without affecting performance of system 40 to any significant degree. Regardless of the exact operational details, the objective is to detect the rotation angle 32 at which sensor module 20 is pointing directly towards source 38. This angle will be referred to as the target rotation angle 32.

According to some embodiments of system 40, radiation detector 22 (FIGS. 3, 5, 6A and 6B) includes at least one first radiation detector 22A and at least one second radiation detector 22B. These embodiments of system 40 rely upon comparison of output signals 34 from radiation detectors 22A and 22B for each rotation angle 32. A target angle of rotation 32 which produces output signals 34 from radiation detectors 22A and 22B with a known relationship indicates that radiation detectors 22A and 22B are both facing source 38 to the same degree. When radiation detectors 22A and 22B have identical receiving areas, the known relationship is equality. This target angle of rotation 32 is employed to determine a plane in which source 38 resides.

In order to increase the sensitivity of system 40 to small differences between output signals 34 from radiation detectors 22A and 22B it is possible to introduce one or more radiation shields 36 at a fixed angle with respect to radiation detectors 22A and 22B. Radiation Shield 36 causes a magnitude of the component of output signal 34 from first radiation detector 22A and a magnitude of the component of output signal 34 from second radiation detector 22B to each vary with rotation angle 32 (see FIG. 3). Radiation shield 36 differentially shadows either radiation detectors 22A or 22B depending upon the relationship between angles of incidence 39 and 41. At some angle of rotation 32, neither radiation detector 22A nor 22B will be shadowed by radiation shield 36. This angle of rotation 32 is employed to determine a plane in which source 38 resides. This configuration insures that small variations from this target angle of rotation 32 cause relatively large differences in the output signals 34 from radiation detectors 22A and 22B because of the shadow effect. Use of radiation shield 36 in sensor module 20 can increase the sensitivity of system 40. This increased sensitivity permits sensor module 20 to function effectively even with a low number of detectable radioactive counts.

Figure 6A:
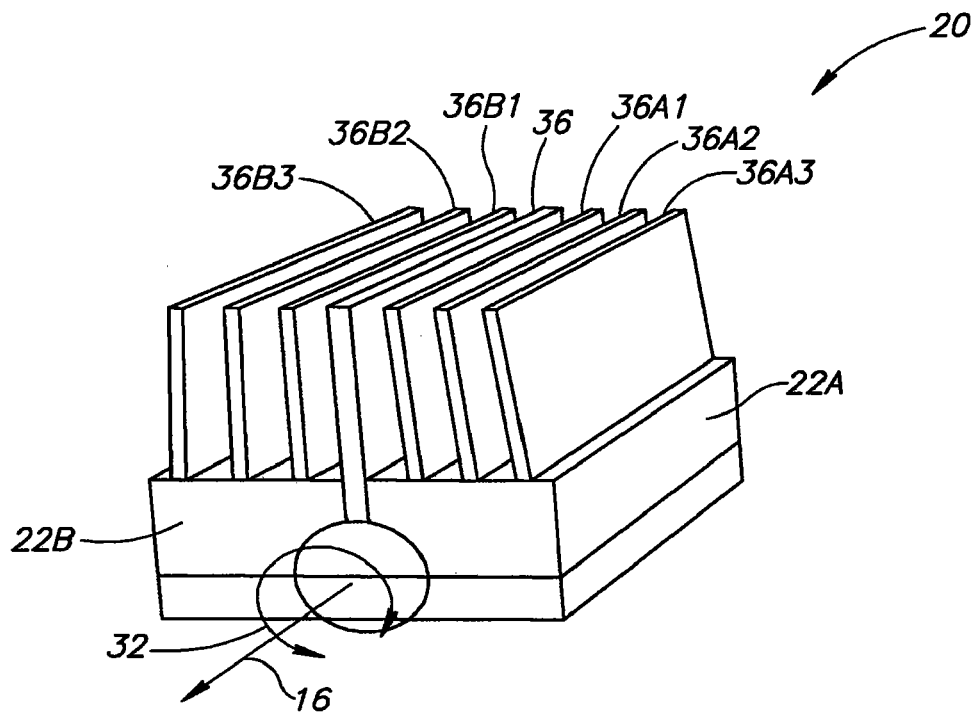
FIGS. 6A and 6B are side views of further additional embodiments of a sensor module according to exemplary embodiments of the present invention.
Figure 6B:
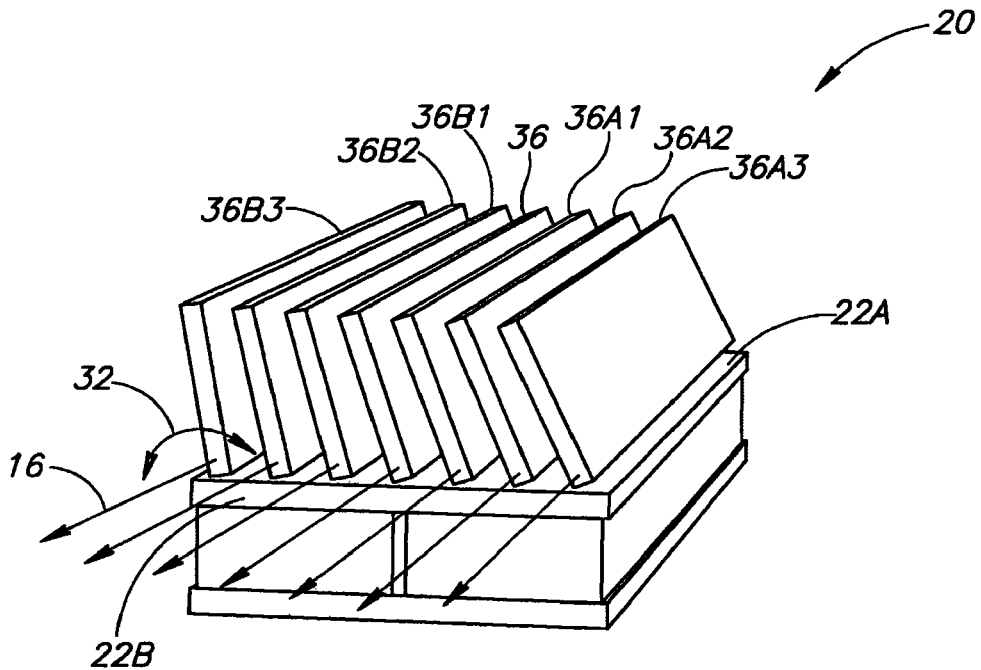

FIG. 6A illustrates an additional embodiment of sensor module 20 in which the radiation shield includes a primary radiation shield 36 located between first radiation detector 22A and second radiation detector 22B. The picture embodiment also includes a series of first additional radiation shields (36A1, 36A2, and 36A3) which divide first radiation detector 22A into a series of first radiation detectors and interfere with incident radiation directed towards first radiation detector 22A. The pictured embodiment also includes a series of second additional radiation shields (36B1, 36B2, and 36B3) which divide second radiation detector 22B into a series of second radiation detectors and interfere with incident radiation directed towards second radiation detector 22B. This configuration can insure that even smaller variations from target rotation angle 32 cause relatively large differences in the output signals 34 from radiation detectors 22A and 22B by increasing the shadow effect in proportion to the number of additional radiation shields (36A1, 36A2, 36A3, 36B1, 36B2, and 36B3 in the pictured embodiment). Use of additional radiation shields (e.g. 36A1, 36A2, 36A3, 36B1, 36B2, and 36B3) in sensor module 20 may serve to achieve an additional increase in sensitivity of system 40. Optionally, secondary radiation shields (36A1, 36A2, 36A3, 36B1, 36B2, and 36B3 in the pictured embodiment) are inclined towards primary radiation shield 36. The angle of secondary radiation shields 36A1, 36A2, 36A3, 36B1, 36B2, and 36B3 towards primary shield 36 can be changed, for example, using a motor to improve focus and/or define imaging volume.

A similar effect may be achieved by holding radiation detectors 22A and 22B at a fixed angle and subjecting radiation shield(s) 36 (FIG. 6B) to angular displacement. System 40 is optionally provided in an embodiment in which radiation detector 22 includes at least one first radiation detector 22A and at least one second radiation detector 22B and output signal 34 includes discrete components from detectors 22A and 22B with at least one radiation shield 36 rotatable about an axis of shield rotation through an angle of shield rotation 32 so that a magnitude of discrete components of output signal 34 from detectors 22A and 22B each vary as a function of the angle of shield rotation 32. Axes 16 are used to indicate to individual rotation axes of each radiation shield. Optionally, the radiation shields are rotated as a group to track the source, instead of rotating the sensor itself. Optionally, the radiation shields are rotated to adjust an aim of the sensor, for example, to modify a depth range and/or a focus point and/or dispersement. Optionally, adjustment is using a screw, optionally manual, optionally using an actuator. Optionally, a controller is used to adjust focusing and/or aiming depending on the movement of the source relative to the sensor. Optionally, as described below, a template, such as a slotted plate, is used to position the radiation shields.

Figure 5:
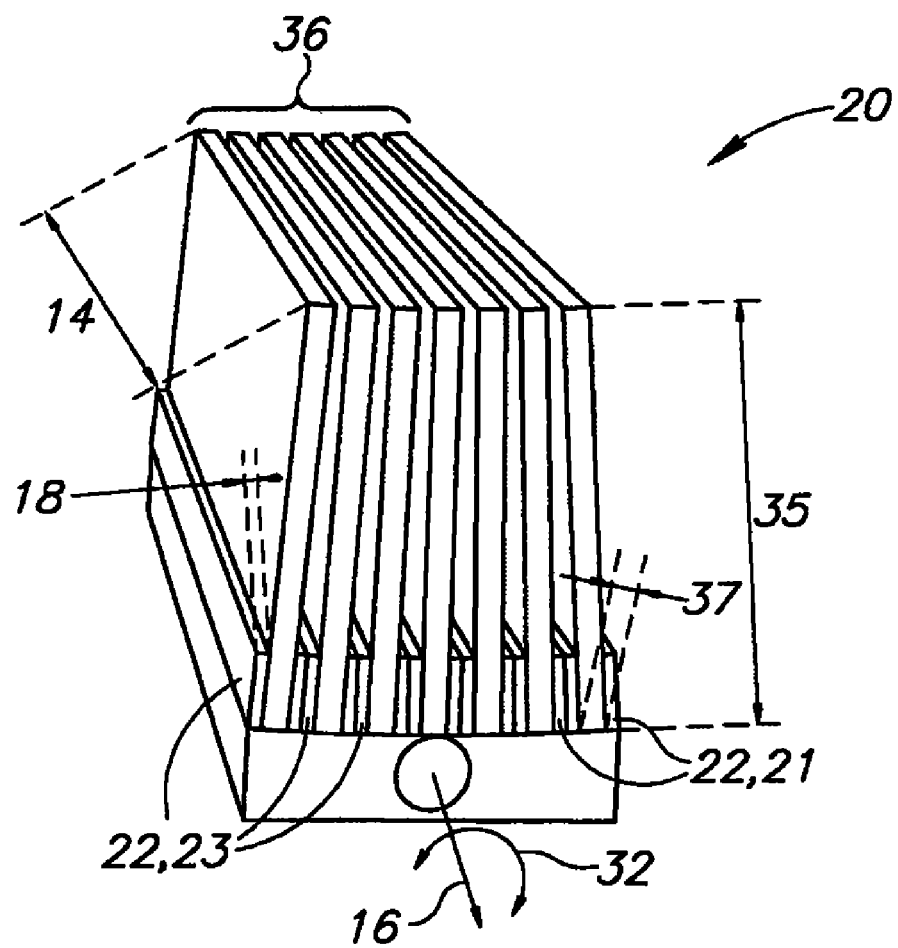
FIG. 5 is a side view of another additional embodiment of a sensor module according to an exemplary embodiment of the present invention.

Referring now to FIG. 5, alternate embodiments of sensor module 20 of system 40 are configured so that radiation detector 22 includes a plurality of radiation detectors 22 and a plurality of protruding radiation shields 36 interspersed between the plurality of radiation detectors 22. According to these embodiments, plurality of radiation detectors 22 is organized in pairs, each pair having a first member 21 and a second member 23 and each protruding radiation shield 36 of the plurality of protruding radiation shields is located between first member 21 and second member 23 of the pair of radiation detectors 22. According to this embodiment, sensor module 20 is capable of rotating the radiation detectors 22 through a series of rotation angles 32 so that the receiving the radiation from radiation source 38 upon radiation detectors 22 varies with rotation angle 32. Each radiation detector produces an output signal 34. CPU 42 sums output signals 34 from all first members 21 to produce a first sum and all second members 23 to produce a second sum. Assuming that all of radiation detectors 22 are identical, when the sensor is aimed directly at the center of mass of source 38 (target rotation angle 32), the first sum and the second sum are equivalent. This embodiment ensures that the total output for the entire module 20 increases rapidly with even a very slight change in rotation angle 32 in either direction. Alternately, or additionally, the sign of the total output for the entire module 20 indicates the direction of rotation required to reach the desired rotation angle 32. Thus, this configuration serves to increase both speed of operation and overall accuracy of system 40. This type of sensor module 20 may be operated (for example) by implementation of a first algorithm summing gamma ray impacts from source 38 for a period of time and allowing CPU 42 to decide, based on the sign and/or total output for the entire module 20, in which direction and/or to what degree to rotate radiation detectors 22 in an effort to reach a desired rotation angle 32. A variant of this algorithm is described below, with respect to FIG. 13. Alternately, CPU 42 may (for example) implement a second algorithm which rotates radiation detectors 22 a very small amount in response to every detected count. Performance data presented herein is based upon a simulation of the second algorithm, but the first algorithm is believed to be useful, at least for some applications.

In an exemplary embodiment of the invention, the interconnection of the detectors (e.g., in the sensor of FIG. 5) is on an analog level or on a digital level. Optionally, a switching mechanism, for example, suitable multiplexers and/or digital processing, is used to selectively add together or otherwise combine signals detected from individual detectors. In one example, based on a knowledge of the approximate relative positions of the source and sensors; and aiming direction of individual shields, some detector elements are given a higher weight and/or the contribution of some detectors dropped. This may be useful, for example, when different detector elements have different viewing volumes or lines and focus of the sensor as a whole is changed by selecting detectors in accordance. Alternatively or additionally, energy may be detected for each such detector, for example, to discriminate multi-energy sources or multiple sources with different energy (e.g., 2, 3, 4, 5 sources). Optionally, for some embodiments, localization within a detector element is provided, for example, using methods know in the art. This may provide a higher accuracy than provided by the shields alone.

According to additional embodiments of system 40, a single sensor module 20 may be employed to determine two intersecting planes in which source 38 resides. This may be achieved, for example, by revolution of sensor module 20 or by moving sensor module 20 to a new location.

According to some embodiments of the invention, sensor module 20 may be additionally capable of revolving radiation detector 22 about an axis of revolution 25 through an angle of revolution 29. Revolution is produced by a revolution mechanism 27 which may function in a variety of ways as described hereinabove for rotation mechanism 26. According to these embodiments of the invention angle of revolution 29 is included as a component of the orientation of sensor module 20 and is included in output signal 34. Revolution may be employed in the context of any or all of the sensor module 20 configurations described hereinabove and hereinbelow. Revolution may occur, for example, in response to a revolution signal 46 transmitted to sensor module 20 from CPU 42 via channel of communication 48.

According to additional embodiments of the invention, sensor module 20 includes a locomotion device 31 capable of imparting translational motion 33 to module 20 so that the location of module 20 is changed. Locomotion may be initiated, for example, in response to a translational motion signal 46 transmitted to sensor module 20 from CPU 42 via channel of communication 48. According to various embodiments of the invention, locomotion may be used to either permit a single sensor module 20 to operate from multiple locations or to provide angular sensitivity to sensor module 20. In other words, translational motion may be used as a substitute for angular displacement, especially in embodiments which employ at least one radiation shield 36. In embodiments which employ translational motion, translation of a single sensor 20 in a first dimension permits acquisition of a first set of directional information. For example, in the embodiment of system 40 depicted in FIG. 4, successive vertical displacement of sensor 20A could be used to determine a first plane in which source 38 resides. Successive horizontal displacement of sensor 20B could be used to determine a second plane in which source 38 resides. Alternately, or additionally, a single sensor 20 may be subject to both vertical and horizontal displacement. Successive vertical and horizontal displacement permits a single sensor 20 to determine two non-parallel planes in which source 38 resides. Concurrent vertical and horizontal displacement along a single line permits a single sensor 20 to determine a single plane in which source 38 resides. Determination of intersection of 2 or 3 or more planes is as determined above. Optionally locomotion and revolution may be employed in the same embodiment of the invention.

Optionally, system 40 further includes an imaging module 50 including an image capture device 56 capable of providing an image signal 52 to CPU 42. Imaging module 50 optionally includes an interface to facilitate communication with CPU 42. CPU 42 is capable of translating image signal 52 to an image of a portion of the body of subject 54. According to various embodiments of the invention, imaging module 50 may rely upon fluoroscopy, MRI, CT or 2D or multi-plane or 3D angiography. For intracranial procedures, imaging generally need not be conducted concurrently with the procedure. This is because the brain does not shift much within the skull. Images captured a day or more before a procedure, or a few hours before a procedure, or just prior to a procedure, may be employed. According to alternate embodiments of the invention, image data is acquired separately (i.e. outside of system 40) and provided to CPU 42 for alignment.

Alignment methods and the algorithms for anatomical image display and tracking information overlay are reviewed in Jolesz (1997) Radiology. 204(3):601-12. The Jolesz article, together with references cited therein, provides enablement for a skilled artisan to accomplish concurrent display and alignment of image data and tracking data. The Jolesz reference, together with references cited therein, are fully incorporated herein by reference to the same extent as if each individual reference had been individually cited and incorporated by reference.

In an exemplary embodiment of the invention, the location(s) determined by system 40 are registered with respect to the image. This may be accomplished, for example by registering system 40 and/or sensors 20 to image capture device 56.

Regardless of which type of sensor module 20 is employed, system 40 may include a display device 43 in communication with CPU 42. Display device 43 may display the image of the portion of the body of the subject with a determined position of the medical device (corresponding to a position of source 38) superimposed on the image of the portion of the body of the subject. The superimposed determined position is optionally represented as a point on display screen 43. Optionally the point is surrounded by an indicator of a desired confidence interval determined by CPU 42. The confidence interval may be displayed, for example, as a circle, as two or more intersecting lines or as one or more pairs of brackets. Alternately, or additionally, display device 43 may display position coordinates of a determined position of the medical device (e.g., corresponding to a position of source 38 at a tip of guidewire).

Display device 43 may be provided with a 3-dimensional angiography dataset from CT, MRI, or 3-D angiography, imaged either during the procedure or prior to the procedure. Appropriate software can be employed to extract a 3-D model of the vasculature from the angiography dataset, and display this model using standard modes of 3-D model visualization. A 3-dimensional graphical representation of the guidewire or catheter can be integrated into the 3-D model of the vasculature and updated with minimal temporal delay based on the position information provided by system 40 to indicate the position of the guidewire or catheter within the vasculature. The entire 3-D model including the vasculature and the catheter can be zoomed, rotated, and otherwise interactively manipulated by the user during performance of the procedure in order to provide the best possible visualization.

Optionally, system 40 may further include one or more user input devices 45 (e.g. keyboard, mouse, touch screen, track pad, trackball, microphone, joystick or stylus). Input device 45 may be used to adjust an image as described hereinabove on display device 43 and/or to issue command signals to various components of system 40 such as rotation mechanism 26, revolution mechanism 27, locomotion device 31 or image capture device 56.

Figure 3:
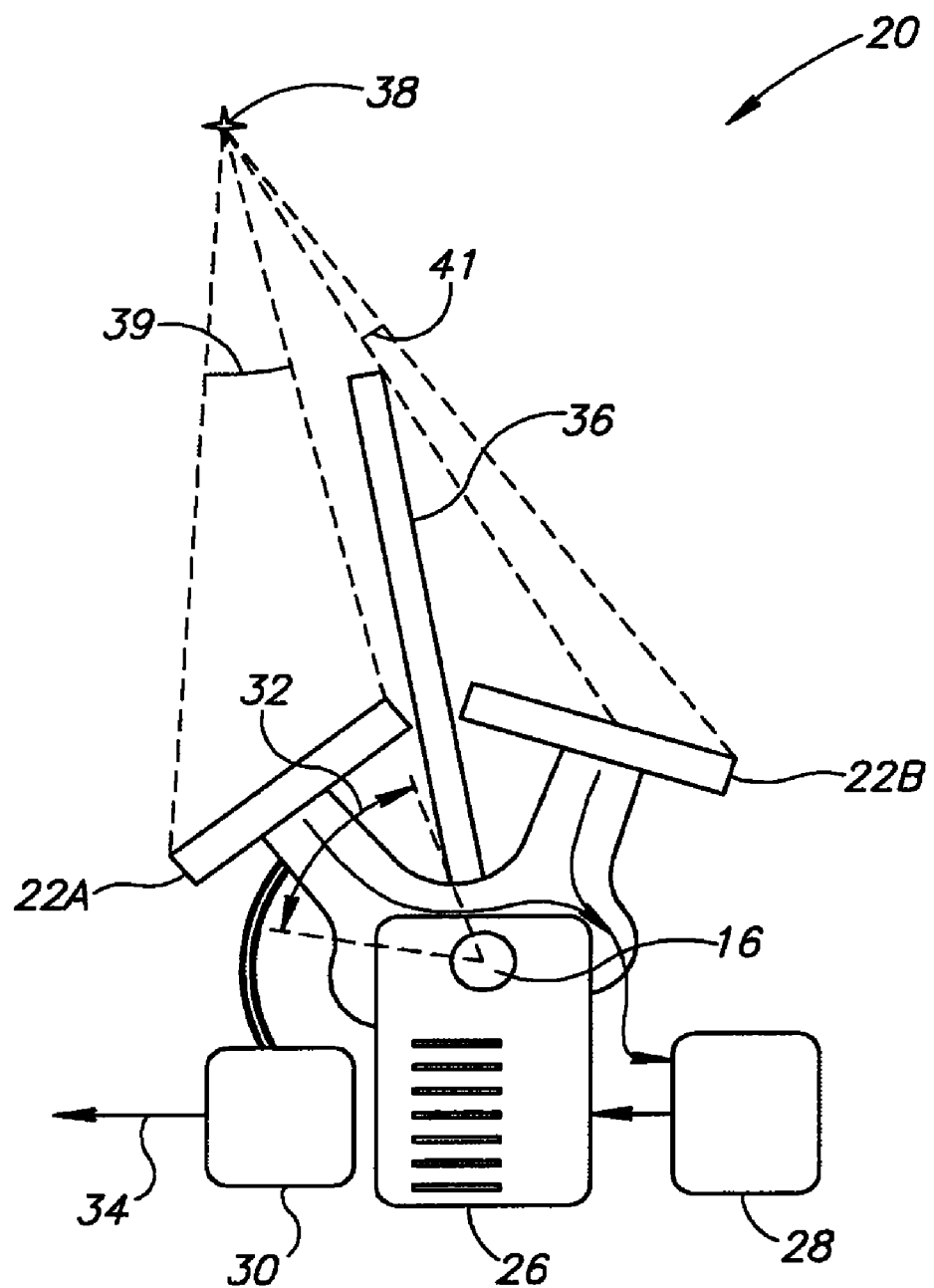
FIG. 3 is a side view of an additional embodiment of a sensor module according to an exemplary embodiment of the present invention illustrating receipt of a signal by the module.

The invention optionally includes a sensor 20 for determining a plane in which a radiation source resides as depicted in FIG. 3 and described hereinabove. Briefly, the sensor 20 includes at least one radiation detector 22, the at least one radiation detector capable of receiving radiation from radiation source 38 and producing an output signal 34. Sensor 20 is capable of rotating radiation detector 22 through a series of positions, each position defined by a rotation angle 32 so that the receiving the radiation from radiation source 38 upon radiation detector 22 varies with rotation angle 32. Rotation is optionally achieved as described hereinabove. A rotation angle 32 which produces a predetermined and/or extreme (e.g., maximum) target output signal indicates the plane in which radiation source 38 resides.

According to some embodiments of sensor 20, radiation detector 22 includes at least one first radiation detector 22A and at least, one second radiation detector 22B and output signal 34 includes a first output signal from first radiation detector 22A and a second output signal from radiation detector 22B.

According to some embodiments of sensor 20, at least one radiation shield 36 is further installed at a fixed angle with respect to detectors 22A and 22B. As a result, a magnitude of the first output signal 34 from the at least one first radiation detector and a magnitude of the second output signal 34 from radiation detector 22B each vary with rotation angle 32 as detailed hereinabove.

A sensor 20 for determining a plane in which a radiation source resides and characterized by at least one radiation shield 36 rotatable about an axis of shield rotation through an angle of shield rotation 32 as described hereinabove in detail (FIG. 6B) is an additional embodiment of the invention.

Sensor 20 for determining a plane in which a radiation source resides as depicted in FIG. 5 and described hereinabove is an additional embodiment of the invention.

Figure 11:
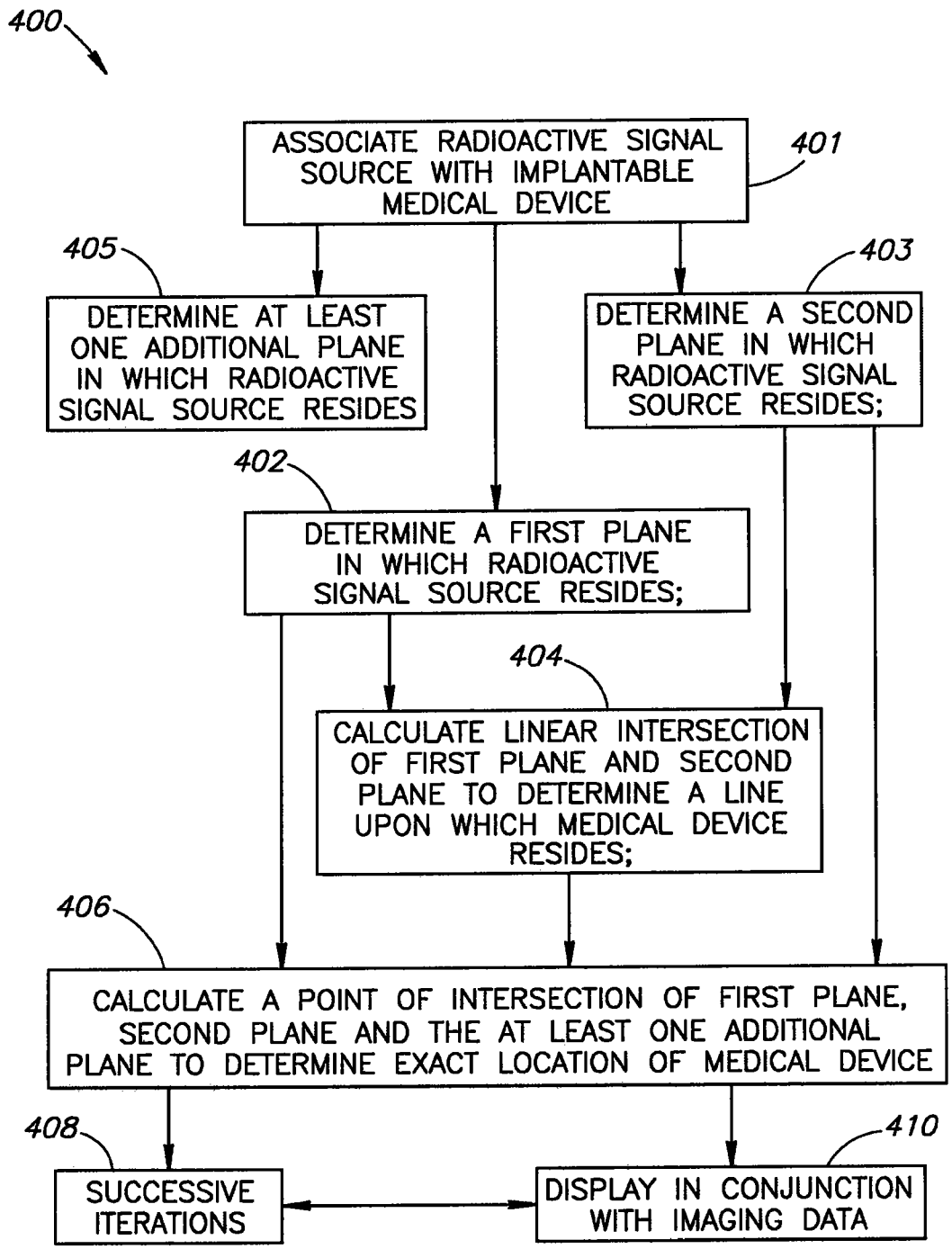
FIG. 11 is a simplified flow diagram of a method according to exemplary embodiments of the present invention.

According to alternate embodiments of the invention, a method 400 (FIG. 11) of determining a location of a medical device within a body of a subject is provided. Method 400 includes co-localizing 401 a radioactive signal source 38 with a medical device. Co-localization may be achieved, for example, by providing a device having a radiation source associated therewith or by associating a radiation source with a device.

Method 400 further includes determining 402 a first plane in which the omni directional signal generator resides, further determining 403 a second plane in which the omni directional signal generator resides, calculating 404 a linear intersection of the first plane and the second plane as a means of determining a line upon which the medical device resides.

Method 400 optionally includes further determining 405 at least one additional plane in source 38 resides.

Method 400 optionally includes calculating 406 a point of intersection of the first plane, the second plane and the at least one additional plane as a means of determining a location of the medical device.

Optionally, method 400 is successively iterated 408 so that a series of locations are generated to track an implanted medical device in motion. Calculated locations may be displayed 410 in conjunction with anatomical imaging data if desired.

The various aspects and features of system 40 and/or sensors 20 described in detail hereinabove may be employed to enable or enhance performance of method 400.

System 40 and method 400 may employ various mathematical algorithms to compute the location of source 38. One example of an algorithm suited for use in the context of some embodiments of the invention calculates the position of source 38 from sensor output signal 34, sensor position, and sensor orientation of three sensors as follows:

1) the plane defined by each sensor module 20 is calculated using an equation of the form $$Ax+By+Cz=D$$

2) the coefficients A, B, C, and D are calculated as follows:
   a. Three non-collinear points are defined within system 40's internal reference frame.
   b. These three points are then shifted by the position of sensor 20 and rotated by the sensor orientation. This defines the plane in which source 38 would lie if output signal 34 was zero.

c. These three points are then rotated about the axis of rotation angle 32 of sensor 20 by rotation angle 32 indicated by output signal 34. This defines the plane in which source 38 lies as measured by a particular sensor 20.

d. Using the x,y,z coordinates of the three points, x1,y1, z1,x2,y2,z2,x3,y3,z3 in the following equations, A, B, C, and D are calculated as follows:

$$A = y1(z2-z3) + y2(z3-z1) + y3(z1-z2) \qquad \text{i.}$$

$$B = z1(x2-x3) + z2(x3-x1) + z3(x1-x2) \qquad \text{ii.}$$

$$C = x1(y2-y3) + x2(y3-y1) + x3(y1-y2) \qquad \text{iii.}$$

$$D = x1(y2*z3 - y3*z2) + x2(y3*z1 - y1*z3) + x3(y1*z2 - y2*z1) \qquad \text{iv.}$$

3) Calculation of A, B, C, and D for each of three sensors 20 produces a system of three equations in three unknowns:

$$\begin{bmatrix} A1 & B1 & C1 \\ A2 & B2 & C2 \\ A3 & B3 & C3 \end{bmatrix} \begin{bmatrix} x \\ y \\ z \end{bmatrix} = \begin{bmatrix} D1 \\ D2 \\ D3 \end{bmatrix}$$

This system of equations can be solved to provide an exact solution for (x,y,z) (or part of the vector), the point of intersection of the three planes, which is the position of the source 38.

Use of additional sensors 20 improves the accuracy by averaging the errors in the individual sensors, and may also provide a means of estimating the accuracy of the position measurement by indicating the extent to which the sensors agree with each other.

When 4 or more sensors are used, the algorithm is as follows: Steps 1 and 2 above remain the same—the equation of the plane indicated by each sensor is calculated. Step 3 is modified as follows:

3) Once A, B, C, and D have been calculated for each of the sensors an over-determined system of more than three equations in three unknowns results:

$$\begin{bmatrix} A1 & B1 & C1 \\ A2 & B2 & C2 \\ A3 & B3 & C3 \\ \vdots & \vdots & \vdots \end{bmatrix} \begin{bmatrix} x \\ y \\ z \end{bmatrix} = \begin{bmatrix} D1 \\ D2 \\ D3 \\ \vdots \end{bmatrix}$$

This over-determined system can be solved in a least square sense using methods familiar to those skilled in the art in order to obtain the best solution for (x,y,z), which is the most likely position of the tracked element. There is generally no exact solution due to the error in the sensor outputs, there may be no single point through which all of the planes pass.

In order that the least square solution may be based on the error defined by the Euclidian distance between each plane and the solution for (x,y,z), it is necessary to scale all of the coefficients defining each plane by the lengths of their respective Normal vectors (the Normal vector is the vector defined by (A,B,C)). This is done by dividing A, B, C, and D by sqrt ($A^2 + B^2 + C^2$) before performing the least square solution.

4) The Euclidian distance between each of the planes and the calculated position can be used as a measure of the accuracy of the position measurement. Once the coefficients have been scaled by the length of the Normal vector, this distance can be calculated for each sensor as Ax+By+Cz−D. The mean value of the distances from each plane to the calculated position gives a measure of the extent to which all of the sensors agree on the position that was calculated.

Overdetermined systems of equations may be solved using least square solution algorithms. Suitable least square algorithms are available as components of commercially available mathematics software packages.

Optionally, other methods of solving equation sets as known in the art are used. Optionally, instead of a set of equations, other calculation methods are used, for example, neural networks, rule based methods and table look up methods in which the signals from the sensors are used to look-up or estimate a resulting position. In systems where the sensors move linearly, other solution methods may be used, for example, translating linear positions of the sensors into spatial coordinates of the source.

In order to increase the accuracy and performance of system 40 and method 400, advance calibration may optionally be performed. The position and orientation of each of the sensor modules 20 can be calibrated instead of relying upon values based on the mechanical manufacturing of the system. The calibration procedure involves using system 40 to measure the 3-dimensional position of a source 38 at a number of known positions defined to a high degree of accuracy. Since the position of source 38 is known, the equations normally used to calculate the positions (described above) can now be used with the sensor positions and orientations as unknowns in order to solve for these values. Various minimization procedures are known in the art. The number of measurements needed to perform such a calibration may depend on the number of sensor modules 20 in system 40, since it is useful to make enough measurements to provide more equations than unknowns. This calibration procedure also defines the origin and frame of reference relative to which system 40 measures the position of the source, and can optionally provide alignment between the tracking system and another system to which it is permanently attached, such as a fluoroscopy system or other imaging system.

In an exemplary embodiment of the invention, once a position of the source is known, the sensors can remain aimed at the source and not change their orientation. Optionally, if the source moves, determined for example, by a significant change in detected radiation (e.g., a drop of 30%, 50%, 70%, 90% or a greater or intermediate drop), the sensor is moved to scan a range of angles where the source is expected to be. Optionally, the sensor generates a signal indicating on which side of the sensor the source is located, for example as described below. Optionally, the range of scanning depends on an expected angular velocity of the source, for example, based on the procedure, based on the history and/or based on a user threshold. If scanning within the range fails, the range is optionally increased. Optionally, for example as described below, the sensor generates a signal indicating the angular offset of the source.

Optionally, if multiple target sources are provided (e.g., ones with different count rates and/or different energy of emission), the sensors jump between target angles. Optionally, a steady sweep between a range of angles encompassing the two (or more) sources is provided. Optionally, sweeping is provided by ultrasonic or sonic vibrations of the sensor or part thereof, for example, comprising a range of angles 1, 5, 10, 20, 50 or more times a second. Optionally, the amplitude of the vibration determines the range of angles. Optionally, the sensors or sensor portion is in resonance with one or more vibration frequencies.

Optionally, scanning of the sensors, at least in a small range of angles, such as less than 10 or less than 5 or less than 1 degree, is provided even when the sensor is locked on a target source.

The tracking accuracy of system 40 using Iridium-192 as source 38 as described hereinabove has been evaluated only by computer simulation. The simulation is a model of the random distribution of gamma photons emitted by a source 38 within a model head and absorbed by the photon-sensitive elements 22 in a compound differential sensor unit 20 of the type illustrated in FIG. 5. According to the simulation, radiation detector 22 of sensor module 20 rotates so that a new rotation angle 32 is defined every time a photon is absorbed by detector 22. If the photon is absorbed by a positive radiation detector 21 then radiation detector 22 of sensor module 20 rotates in the positive direction, and if it is absorbed by a negative sensor 23 then radiation detector 22 of sensor module 20 rotates in the negative direction. Total output signal 34 of sensor module 20 is its average orientation during the sample time.

According to the simulation, performance is defined by two parameters, however other parameters may be used in a practical system:
1) The Root Mean Square (RMS) error when the target is stationary
2) The time to indicate a 9 mm change in calculated location after a 10 mm change in actual location of source 38.

The following parameter values are fixed in the simulation:
1) Distance from the source to the sensor=25 cm (worst case distance)
2) Source distance for which sensor is geometrically optimized=25 cm
3) Width of photon-sensitive surface in each sub sensor=2 mm (18 in FIG. 5)
4) Sensor length=10 cm (14 in FIG. 5)
5) Height of dividing walls between sensors=5 cm (35 in FIG. 5)
6) Width of dividing walls at their base=4 mm (37 in FIG. 5)
7) Number of subsensors defined by walls in the compound sensor=7 (36 in FIG. 5)
8) Sensor sensitivity (fraction of incoming gamma rays which are detected)=0.3

The simulation evaluated and optimized the following parameters with respect to influence on performance:
1) Rotation magnitude per absorbed photon (FIGS. 7A and 7B)
2) Sample time (FIGS. 8A and 8B)
3) Photons per second (source activity level) (FIGS. 9A and 9B)

Figure 7A:
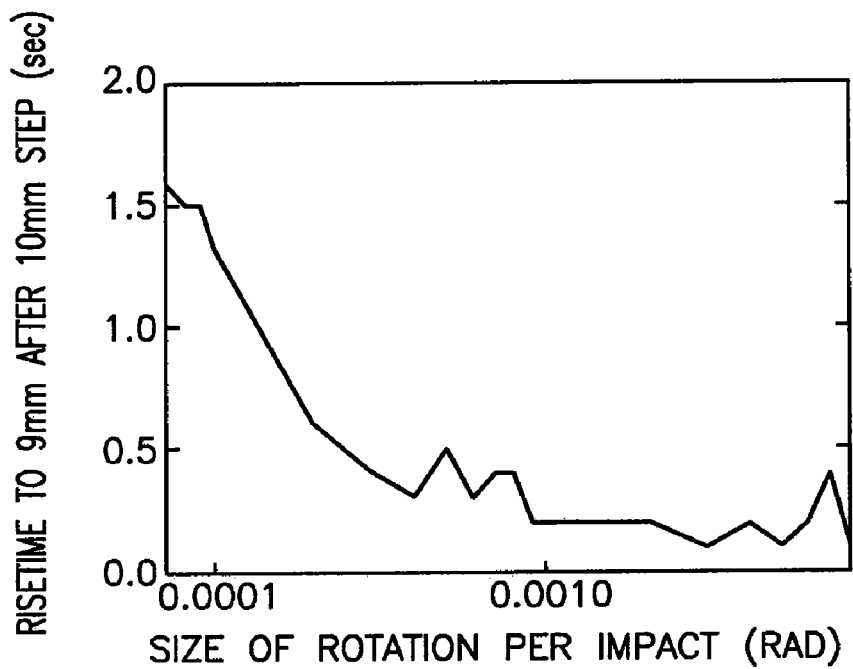
FIGS. 7A and 7B are graphs of simulated response time and simulated rms position error respectively plotted as a function of sensor rotation per photon impact using a system according to an exemplary embodiment of the present invention.
Figure 7B:
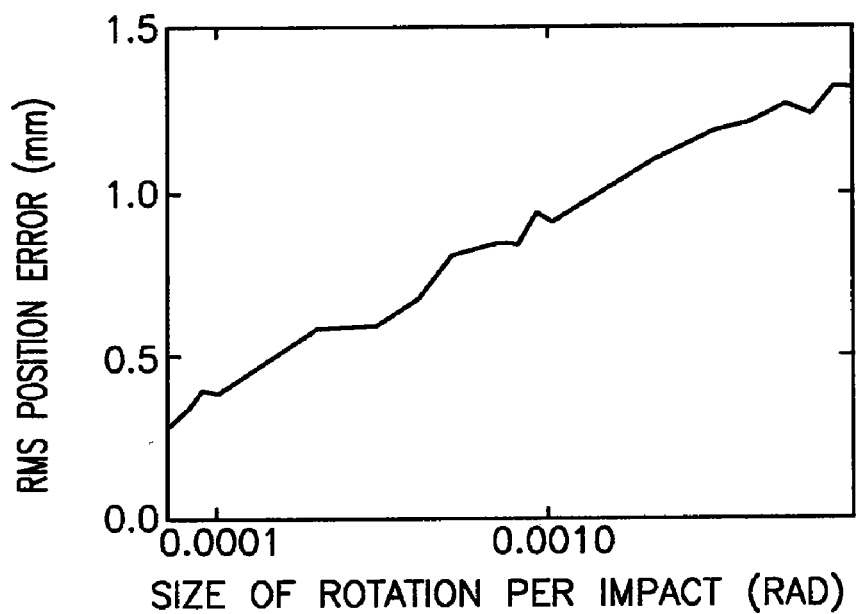

The performance parameters are measured on a simulated movement scenario (FIGS. 10A and 10B). The simulation determined that as rotation per photon impact increases, response time is improved (FIG. 7A). However, as rotation per photon impact increases, RMS position error also increases (FIG. 7B). There is clearly a trade-off between latency and accuracy. This parameter can be modified in real-time in order to optimize the trade-off using a motion detection algorithm as described hereinbelow.

Figure 8A:
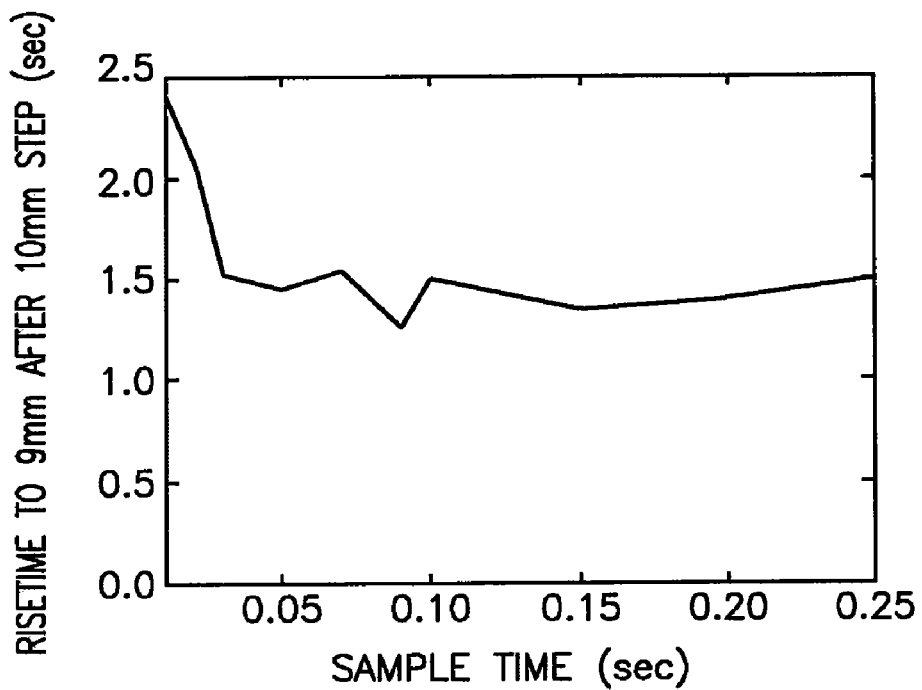
FIGS. 8A and 8B are graphs of simulated response time and simulated rms position error respectively plotted as a function of sampling time using a system according to an exemplary embodiment of the present invention.
Figure 8B:
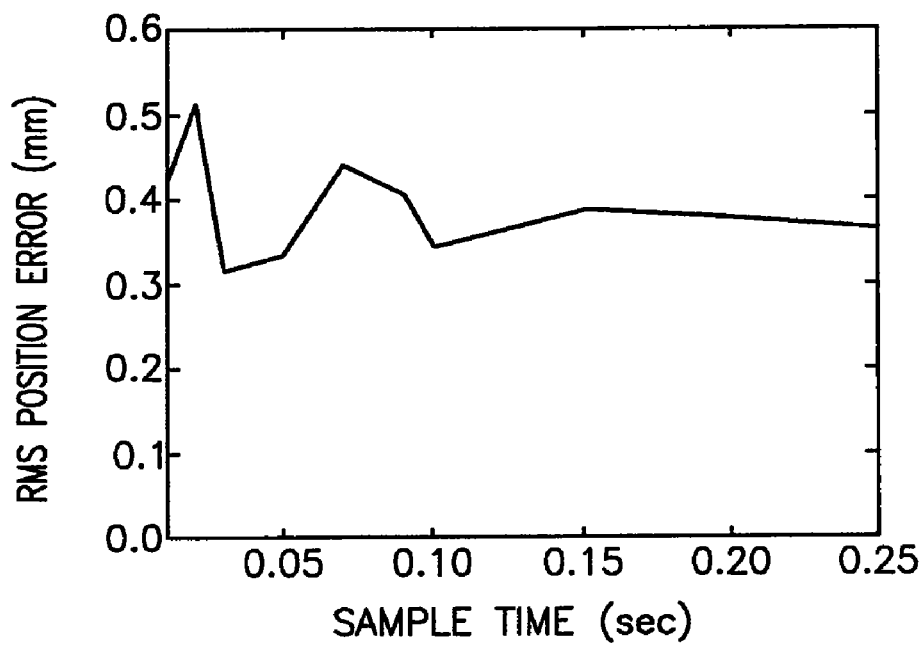

The simulation determined that sample time has no significant impact on latency or accuracy (As shown, for example in FIGS. 8A and 8B). This may be because for small values of rotation per impact, the number of impacts per sample has minimal effect on accuracy and only determines the latency (the total amount of rotation per sample). However, if the number of impacts per sample is reduced as a result of a reduction in the sample time, then the reduction in sample time exactly compensates for the reduced response per sample leaving the latency unchanged.

Radioactivity (number of photons emitted per second) has a very slight effect on accuracy, improving accuracy only by a factor of 2 as the activity increases from 0.01 mCi up to 0.5 mCi (FIG. 9B). It has a drastic effect on response time at low activity levels (FIG. 9A) where there simply are not enough photons to induce rapid rotation, however at activity levels above 0.1 mCi there is minimal improvement with increased activity level. Optimization of this trade-off between latency and accuracy (see below) is achieved with 0.05 mCi. This specific activity provides a good compromise between performance and radiation dose, providing a performance suitable for a typical medical application without imposing a safety risk to the patient or doctor.

In order to optimize the tradeoff between accuracy and latency a motion detection algorithm was employed to increase the rotation per photon during motion of tracked source 38. This decreased latency time and increased accuracy. In the simulation, the percentage of photons hitting receiving elements 22 classed as positive 21 versus those classed as negative 23 was used as an indication of motion of tracked source 38. As the percentage moved farther away from 50% the rotation per photon was increased, reducing latency at the expense of accuracy during motion. In other words, system 40 begins by moving towards an estimated target rotation angle 32 in large steps. As estimated target rotation angle 32 is approached, the size of the steps is decreased. If target rotation angle 32 is passed, a small compensatory step in the opposite direction is employed. Results are summarized graphically in FIGS. 10a and 10b. Briefly, the RMS error of system 40 tracking a moving source 38 is 0.71 mm on average. Location of a stationary source 38 by system 40 produces an rms error of 0.62 mm.

In summary, the simulation results indicate that with an activity of 0.05 mCi of 192Ir, compound differential sensors of the type illustrated in FIG. 5, and a motion detection algorithm which trades-off latency against accuracy, system 40 can achieve overall accuracy of approximately 1 mm RMS.

Figure 12:
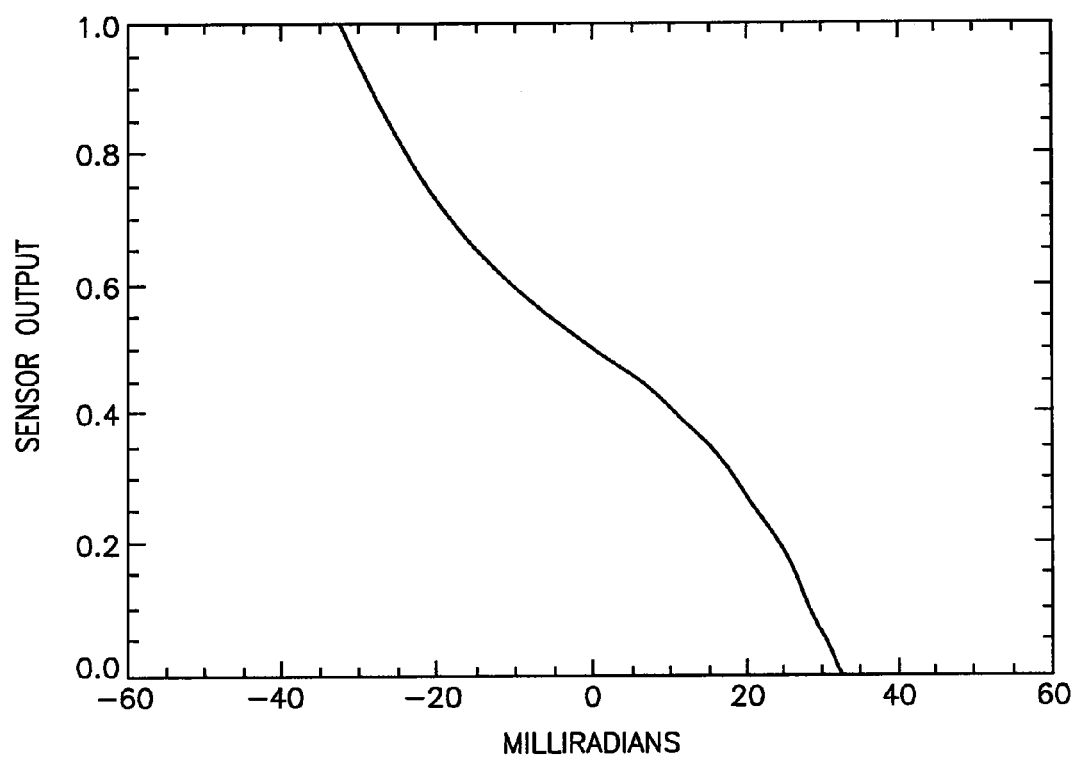
FIG. 12 is a graph of sensor output as a function of rotation angle.

Simulated sensitivity of sensor module 20 to changes in rotation angle 32 is illustrated in FIG. 12 which is a plot of output signal 34 as a function of rotation relative to target rotation angle 32 for a sensor of the type indicated in FIG. 5. The graph was produced using the formula:

$$\text{Total Output } 34 = A/(A+B)$$

Where A is the sum of all right side sensors 21; and
B is the sum of all left side sensors 23.

The total range of output 34 (Y axis) from sensor 20 was arbitrarily defined as being in a range from 0 to 1. On the X axis, 0 indicates the angle of rotation 32 which indicates the direction of source 38. The total rotational range of sensor 20 was ±32 milliradians from this target rotation angle 32. Deviation of more than 32 milliradians away from target rotation angle 32 produced an output 34 of either 0 or 1, indicating the direction of rotation for a return to target rotation angle 32, but not the amount of rotation to reach target rotation angle 32. When output 34 is 0 or 1, the only conclusion that can be drawn about deviation from target rotation angle 32 is that it is greater than 32 milliradians in the indicated direction.

The graph of FIG. 12 depicts output 34 for target rotation angle 32 as the middle of the dynamic range (0.5). If output 34 is 0.4, a correctional rotation of 10 milliradians in the plus direction is indicated to achieve target rotation angle 32. An output 34 of 0.6 indicates a correctional rotation with the same magnitude (10 milliradians), but in the minus direction. Another way of depicting the same information would be to indicate a total dynamic range of +0.5 to −0.5 on the Y axis. This middle of the range could be zero, with one direction being positive and the other negative, or it can be any arbitrary number, with one direction being higher and the other lower.

As illustrated in FIG. 12, at target angle 32 simulated sensitivity of sensor 20 to rotation is approximately 1% of the dynamic range per milliradian of rotation.

This 1% sensitivity per milliradian is sufficient to provide the desired accuracy (1 mm rms), using a 5 cm×10 cm sensor module 20 with shields 36 having a height 35 of 5 cm interspersed between radiation detectors 22 and located 25 cm from source 38 with an activity of 0.05 mCi. Adjusting accuracy parameters, increasing the size of detectors 22, reducing the distance between sensor 20 and source 38 and increasing the activity of source 38 could each serve to reduce the level of directional sensitivity desired of sensor 20.

Simulation results (not shown) using a sensor 20 of the type shown in FIG. 6A were similar to those described hereinabove.

Figure 17A:
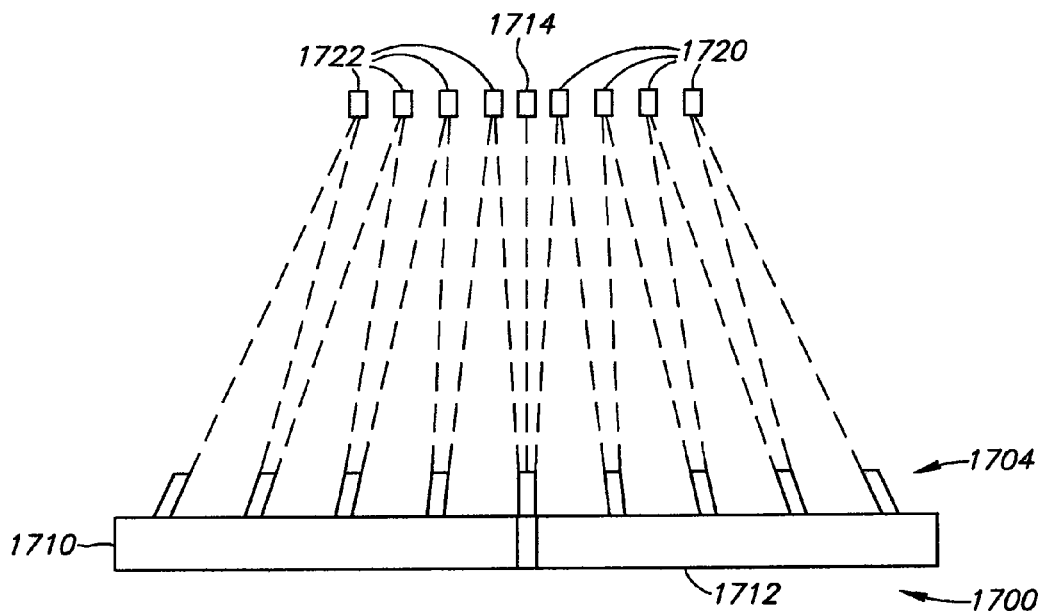
FIG. 17A is a schematic diagram showing multiple non-point focal aiming points for an alternative differential sensor in accordance with an exemplary embodiment of the invention.
Figure 17B:
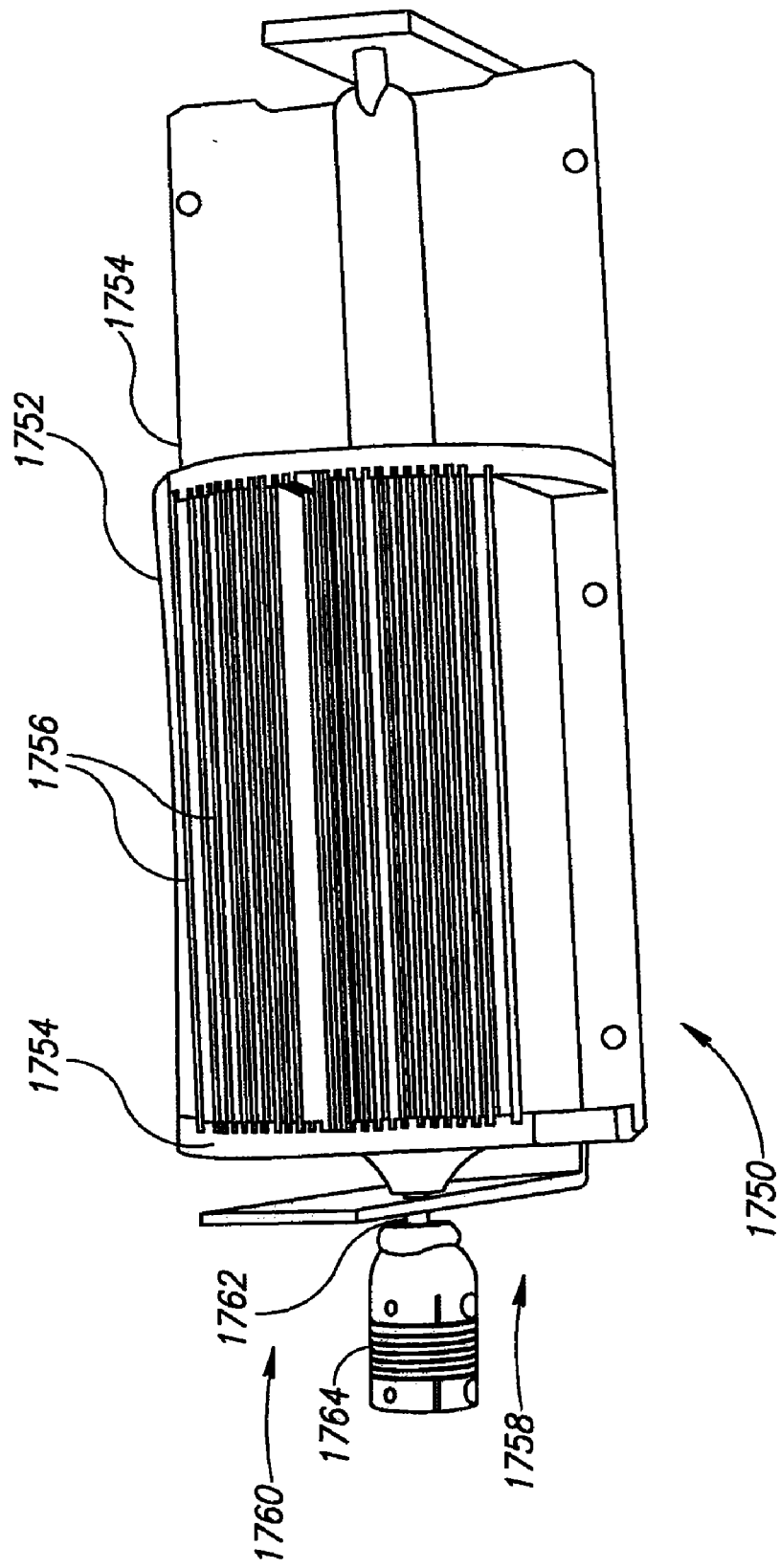
FIG. 17B is a schematic perspective illustration of a sensor showing a collimator design in accordance with an exemplary embodiment of the invention.
Figure 17C:
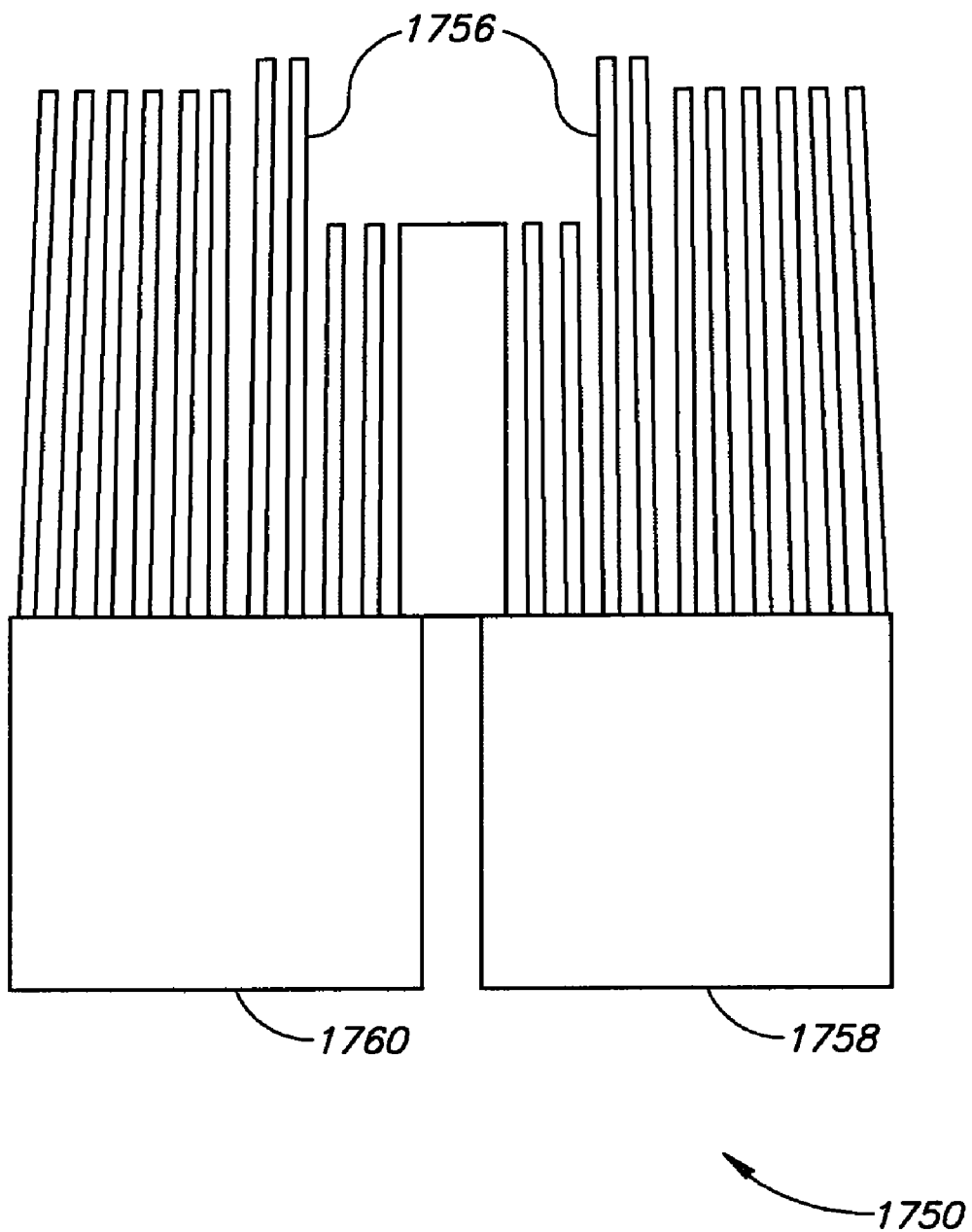
FIG. 17C is a side view of the collimator of FIG. 17B, showing the relative angles and lengths of slats, in accordance with an exemplary embodiment of the invention.
Figure 22:
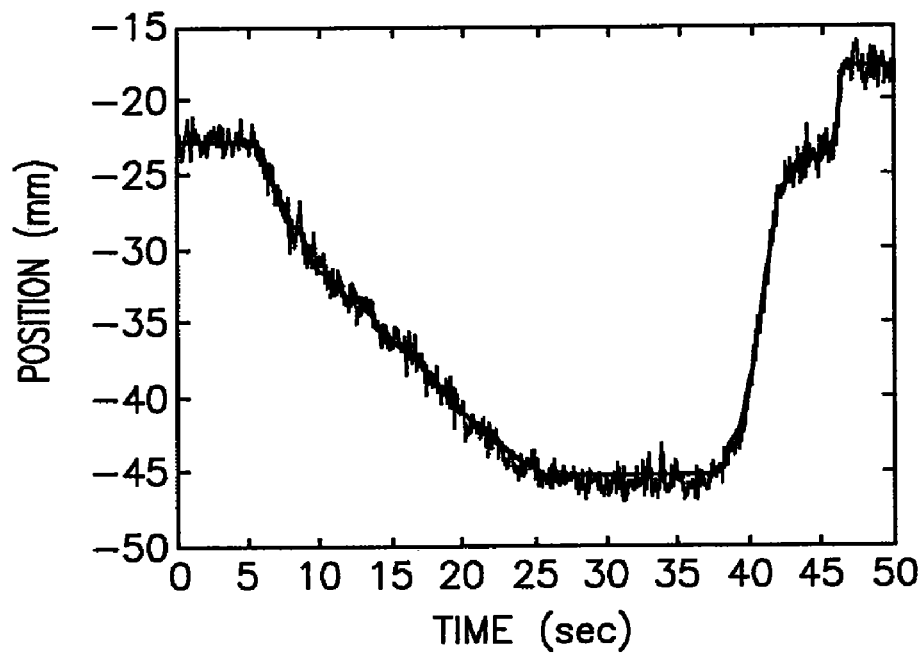
FIGS. 22 and 23 show a real vs. a measured position and error, in an experiment in accordance with an exemplary embodiment of the invention.
Figure 23:
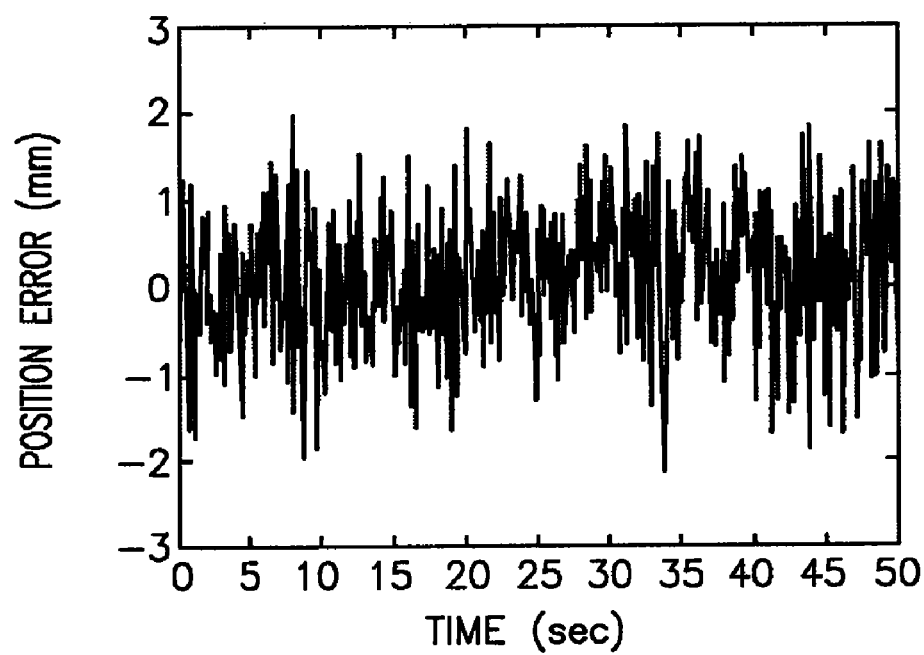

FIGS. 22-23 show results of an actual experiment, using a collimator as described with respect to FIGS. 17B and 17C, and a 1 mm spherical source having 70 µCi of Co57.

Referring to FIG. 22, the smooth line is the actual path, with the jagged line indicating an overlay of the path reconstructed from a signal detected as described herein.

FIG. 23 shows only the error between the actual motion and the reconstructed motion, which error is always smaller than 2 mm and most of the time smaller than 1 mm.

Figure 13:
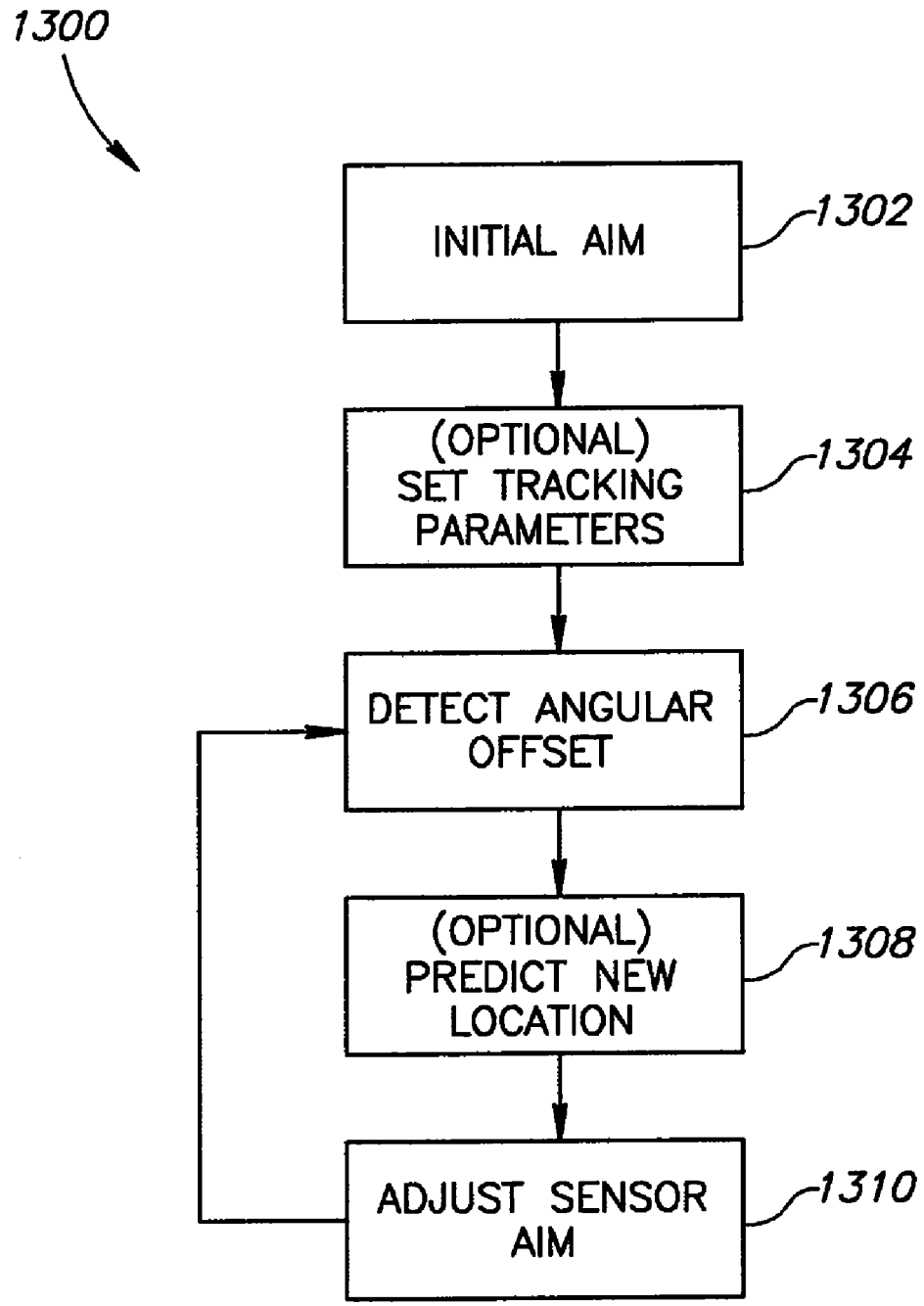
FIG. 13 is a flowchart of a method of tracking a radioactive object based on angular indication, in accordance with an exemplary embodiment of the invention.

FIG. 13 is a flowchart 1300 of a method of tracking a radioactive object (38, FIG. 3) based on an angle offset indication, in accordance with an exemplary embodiment of the invention. It is noted that while the description focuses on a single (two element) sensor, in some embodiments, multiple sensors are controlled simultaneously for example, three orthogonal sensors.

At 1302, the sensor (20, FIG. 3) is aimed at the object. Optionally, the initial aim is manual. Alternatively, the initial aim is by scanning the space using the sensor, for example by rotating or translating the sensor.

At 1304, tracking parameters are optionally set. For example, the tracking parameters may include the expected maximum velocity of the object or its radiation level and/or a sensitivity plot of the sensor.

At 1306, the sensor generates a signal indicating an angular offset between the aiming line of the sensor and the object.

At 1308, the location of the object in the future is optionally predicted. Optionally, the prediction relates to the estimated time it will take the sensor to be realigned. Optionally, the sensor control mechanism is designed for a certain expected angular motion rate. This can allow a slower control mechanism to be used. Various estimation methods are known in the art and may be used.

At 1310, the sensor aim is adjusted, for example according to the offset and/or the predicted position. In the former, the sensor will generally lag behind the source. In the latter, the sensor may lag or be advanced, depending on the correctness of prediction.

In an exemplary embodiment of the invention, the range of angular positions and the speed of angular change of the sensor are selected so that the sensor can track a moving object (e.g., maintain inside the angular range), where the maximum speed is known. Possibly, the sensor is never aimed exactly at the object.

Figure 14:
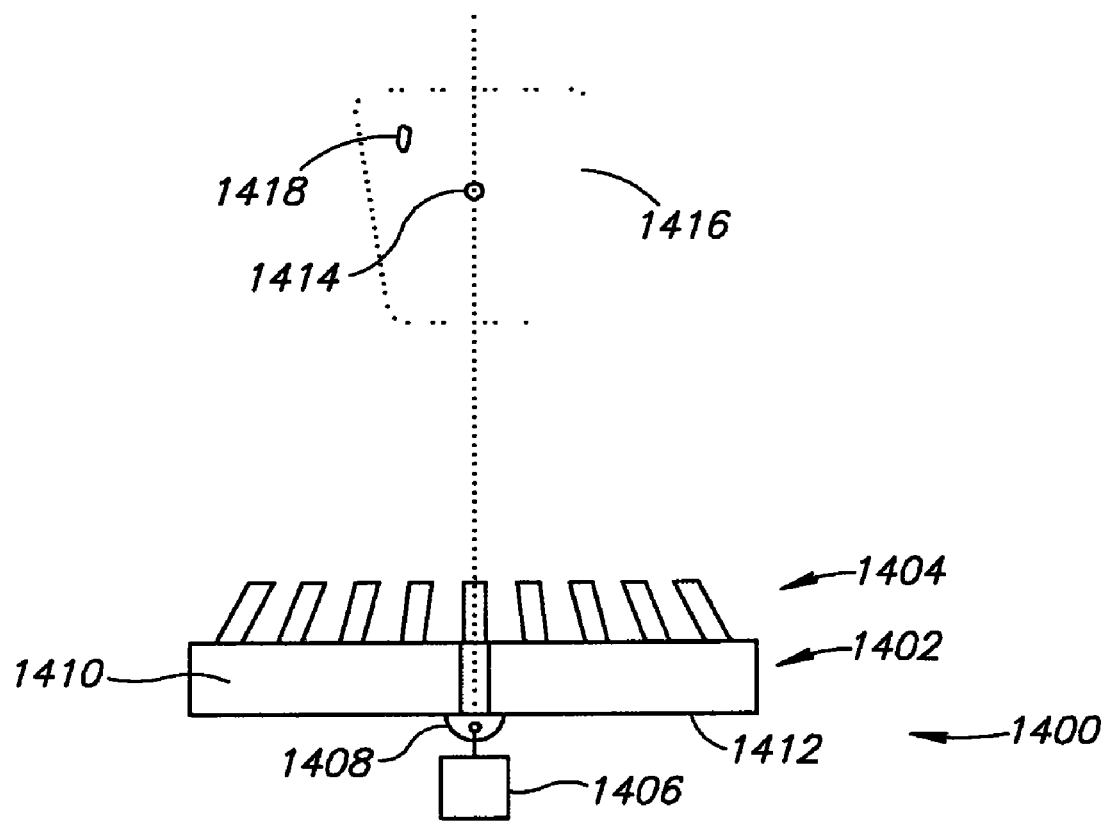
FIG. 14 is a schematic figure showing a spatial relationship between a tracked object and an aiming point of a sensor, in accordance with an exemplary embodiment of the invention.

FIG. 14 is a schematic figure showing a spatial relationship between a tracked object 1418 and an aiming point 1414 of a sensor 1400, in accordance with an exemplary embodiment of the invention.

Sensor 1400 includes a radiation detector 1402, for example a solid state detector, which is divided into at least two sections 1410 and 1412, optionally separated by a space, optionally an extension of the collimator slat. A collimator 1404, which will be described in greater detail below, is optionally provided to shape the sensitivity of the sensor. (This shaping is not illustrated in FIG. 14). Detector 1402 is optionally gimbaled using a hinge 1408 relative to a base 1406.

In an exemplary embodiment of the invention, collimator 1404 is designed so that the sensor is most effective over a limited working volume, for example, that indicated by a dotted area 1416, which includes a range of depths and a range of angles. For simplicity, a 2D collimator and space is shown, the collimator may define a 3D region, for example, if it is a cone-type collimator.

In an exemplary embodiment of the invention, the response of the sensor within this working volume varies in accordance with the angular offset between object 1418 and aiming point 1414 (e.g., relative to sensor 1400), in a manner which allows the angular offset to be reproduced from the response. It should be noted that the shape of the actual working volume will depend on the design of the collimator and may be other than shown, for example, an inverse trapezoid. However, for design purposes, a working volume is defined by a user, for example, a cylinder or a cube. It is within this defined working volume that the angular response is desired. In some cases, the working volume for a sensor is defined by first defining a working volume for a set of sensors (e.g., 3) and then working back to the individual sensors.

While many collimators can have an angle-varying response, this response will often be non-useful in any meaningful area of interest. Some collimator designs could have an angle-varying response, but that response may be spread over too large (or too small) a range of angles and/or too small a range of depths. For example, a highly focused collimator may provide a meaningful angle-dependent signal for only a single depth and a narrow range of angles around it. Referring to the method of FIG. 13, it is desirable in some embodiments of the invention, that the accuracy of the angle determination (e.g., change of signal as a function of change in angle) be relatively uniform (e.g., bounded by a factor of less than 10, less than 5 or less than 2). In an exemplary embodiment of the invention, the design of the collimator and/or detector are selected so that the response will be relatively linear with the angle over a working volume of interest (e.g., dotted area 1416).

Figure 15:
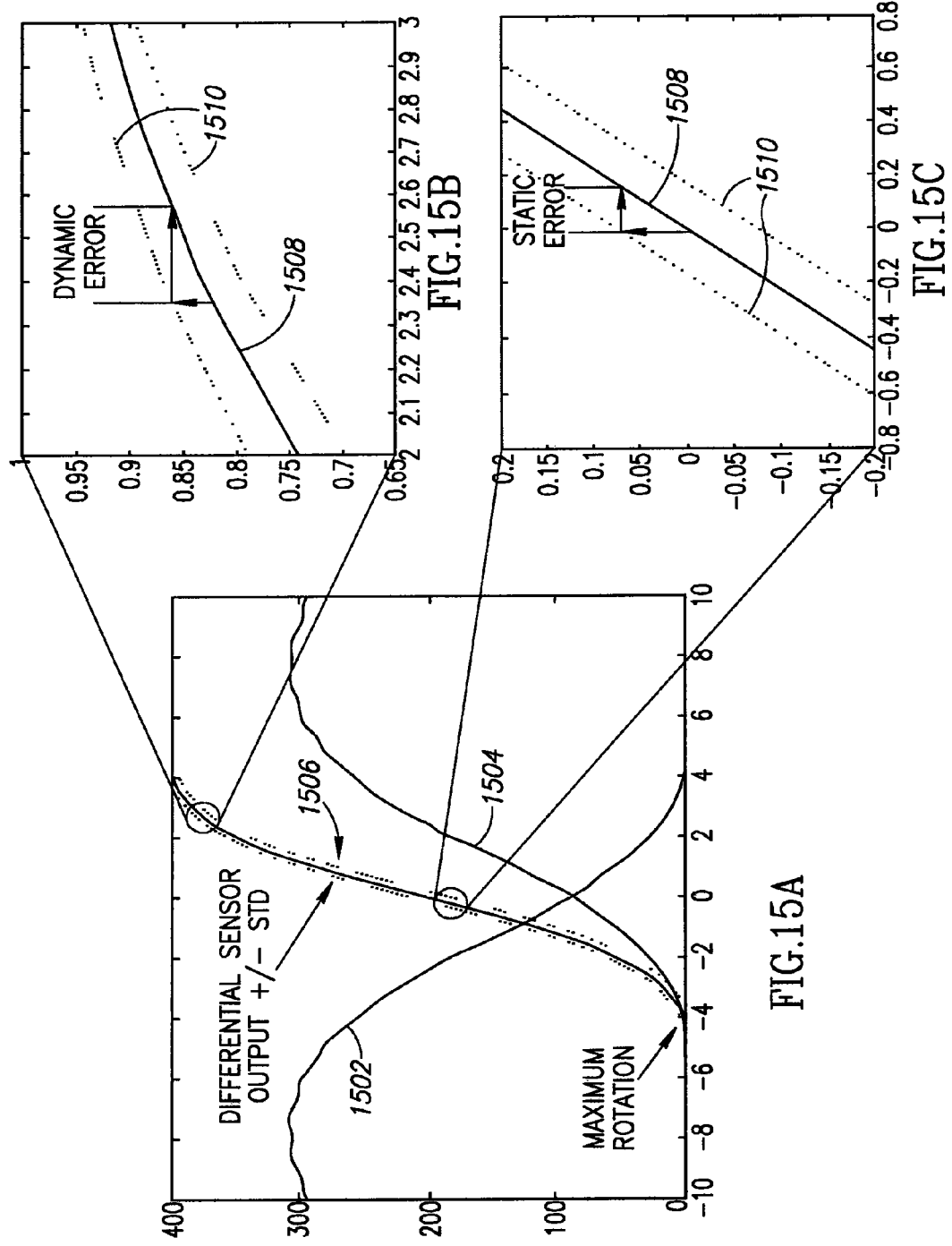
FIG. 15A is a graph showing a simulated angular response of a differential sensor, in accordance with an exemplary embodiment of the invention.
FIGS. 15B and 15C illustrate details of the graph of FIG. 15A.
Figure 16:
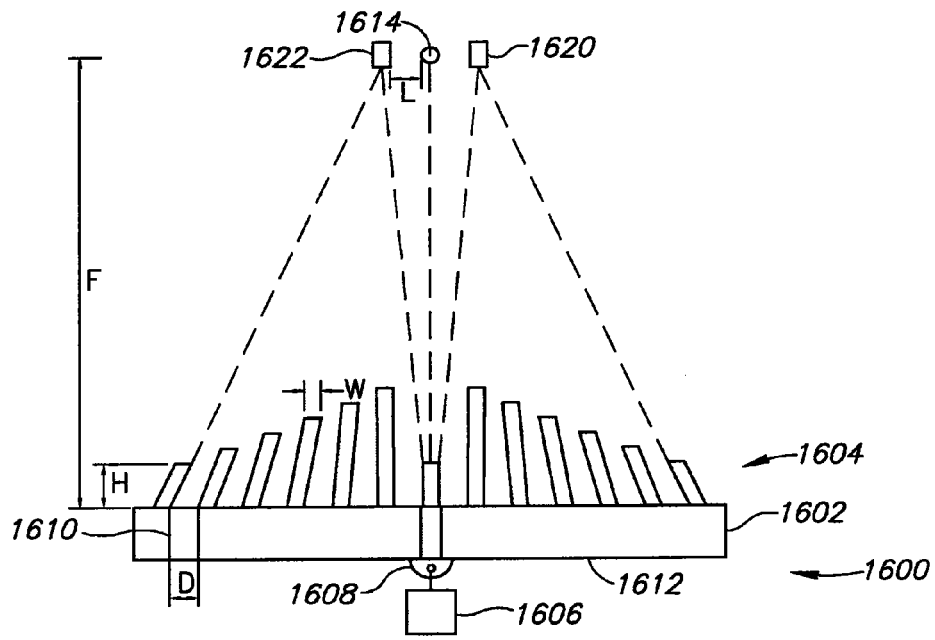
FIG. 16 is a schematic diagram showing multiple focal aiming points for a differential sensor in accordance with an exemplary embodiment of the invention.

One type of collimator design which has this behavior is illustrated in FIGS. 15-16, with FIGS. 15A-15C illustrating the angular response and FIG. 16 illustrating features of an exemplary design, in which each of two sections 1610 and 1612 has a different aiming (focusing) point (1622, 1620) and the combination of the signals from the two sections is quasi linear over a significant range of angles. As will be described in greater detail below, a collimator design for achieving a desired effect is optionally generated and/or selected by an optimization process. While the optimization process is described in greater detail with respect to FIG. 18, some details of exemplary optimization processes are described with reference to FIGS. 15 and 16, to which optimization may be applied. It is generally desirable that the function be monotonic, to prevent confusion; however, this is not essential, for example, for step-wise non-monotonic functions.

The performance of a single collimated sensor is generally defined by the shape and amplitude of the plot of the detected signal versus angle of the source. The shape of the plot determines the theoretical sensitivity of the collimated sensor, and the amplitude determines how accurately the measurement will correspond to the theoretical sensitivity, allowing an angle determination to be made from the measurement.

However, when two such collimated sensors are combined into a differential sensor (e.g., FIG. 16), there are a number of additional factors that are optionally taken into account in determining the performance:

1) When combined into a differential sensor, each individual sensor is not at its peak at the zero angle. The collimators are optionally (FIG. 16) designed such that their peaks are off-center and they have a steep slope at the zero angle. By designing the collimators such that their plots cross at the zero angle in this steep region, the difference between them changes sign at the zero angle and has a very steep slope. The location along their individual signal plots at which the two collimator signal plots cross will determine the number of counts per second at the zero angle, which will determine the accuracy with which the sensor can estimate its angle based on the recorded differential signal. (e.g., FIG. 15).

2) If the sensor is to be used for tracking a moving source (e.g., FIG. 13), then the differential signal is optionally designed to provide accurate information about the angle of the source throughout a range of angles near the zero angle so that this information can be used to adjust the sensor angle appropriately after each measurement to most accurately track the source movement.

3) If the sensor is to be used in a mode in which it actually tracks the movement of a source (e.g., FIG. 13), rather than performing a sweep through a range of angles, then it is optionally useful for the sensor to provide an indication of which direction it must rotate to find the source even when the source is at a very large angle from the zero angle of the sensor. This feature may be implemented by requiring that some small part of each half of the sensor be outside the collimator so that it receives a signal even at very large angles (e.g., FIGS. 5, 6A and 6B).

FIG. 15A shows a composite signal 1506 generated by combining a signal 1502 from section 1610 (FIG. 16) and a signal 1504 from a section 1612 (FIG. 16). FIG. 15B is an enlarged view of the section of composite signal 1506 at a significant angular offset, showing error lines (described below) 1510 and an average value 1508. The error shown is a dynamic error in estimating the angle at positions other than zero offset, i.e., the error when the sensor is not pointed at a single most accurate focal point (as would be the case for a focused fan collimator). FIG. 15C is a similar enlargement for a zero offset angle, showing a static error, i.e., when the sensor is aimed at the source with no offset. FIGS. 15A-15C show the results of a simulation, where the ordinate is in counts and the abscissa is translational offset (equivalent to angle at a distance). Signal 1506 varies over the range −1 . . . +1.

Signal 1506 is generated using a differential sensor output $(a-b)/(a+b)$, where a and b indicate the counts provided by signals 1502 and 1504. The signal is normalized to the count. The accuracy of the source position estimate based on this sensor output generally depends on the number of counts measured by each sensor during the measurement period. The standard deviation of $(a-b)/(a+b)$ is calculated as:

$$std = \frac{1}{\sqrt{a+b}} \times \sqrt{1 - \left(\frac{a-b}{a+b}\right)^2}$$

It should be noted that this equation is only considered to be accurate when a+b is greater than 30 (e.g., that a Poisson distribution approaches the shape of a Gaussian distribution).

Lines 1510 show one standard deviation.

In an exemplary embodiment of the invention, the angular range of a sensor is defined as a maximum rotation, defined, for the left side of the graph, as the distance from the zero point until the smaller of two points; 1) the point at which a+b falls below 30, or 2) the point at which the sensor output +/−one standard deviation reaches +/−1. Generally, the maximum rotation per measurement should be at least as large as the maximum source movement per measurement (maximum source speed) in order to enable an estimate of the dynamic error at the maximum source speed. However, this is not essential and may depend on the application.

The dynamic error is optionally defined as the maximum error within the range of +/−maximum source movement per measurement. The dynamic and static errors for any signal output are defined as the maximum position error that would result, when the source is off-center or on-center respectively, from a signal output of the current signal output +/−one standard deviation.

In an exemplary embodiment of the invention, a collimator/sensor design is defined by a cost function which indicates a quality of the design for the parameters of maximum rotation angle, dynamic error and static error, for example, cost function=static error*static error weight+dynamic error*dynamic error weight+maximum rotation factor Optionally, a noise level (and/or other error factors) is factored into the cost function, for example, as part of the error estimation.

In order to ensure that the maximum rotation remains large enough to enable measurement of the dynamic error, the cost function optionally becomes very large when the maximum rotation falls below the maximum source movement per measurement. Optionally, the maximum rotation factor is 0 when the maximum rotation is above the range of source movement per measurement and very quickly becomes extremely large when the maximum rotation is below the maximum source movement per measurement.

Referring again to FIG. 16, parts 1606 and 1608 correspond to parts 1406 and 1408 of FIG. 14. A virtual aiming point 1614 is shown, however, no part of the sensor is adjusted for this point. Instead, part of the sensor is aimed at a left aiming point 1622, which has an offset, for example, 1-7 mm from point 1614 (in a direction perpendicular to the aiming direction) and part of the sensor is aimed at a right aiming point 1620, offset to the right. It should be noted that for a given depth, angles and translations are interchangeable. As will be described below, the aiming points are optionally part of an optimization process used to define the working volume. While a crossed sensor may be provided, in which the right side looks left and the left side looks right, this will usually not be done due to reduced efficiency and geometrical limitations on slats.

In an exemplary embodiment of the invention, this behavior of the sensor is achieved by having the parts of collimator 1604 overlying the sections 1610 and 1612, each as a separate fan collimator or other focused collimator. FIG. 17A, below, shows a case where each slat has a different angle (aim), with an optional result of a distributed focus.

FIG. 16 shows various collimator parameters which may be adjusted as described below, for example as a result of optimization. "H" is the height of slat, which may vary between slats, for example as shown. "D" is a distance between slats, which may vary in a collimator, for example, as described below. "W" is a width of a slat. While a thinnest slat is generally desirable, a minimum width may be required to provide absorption of radiation and/or structural integrity. "W" may also vary within a collimator. "F" is the distance to aim point 1622. If multiple aim points are provided, F may be different for different aim points. Optionally, a range of effective "F" values is provided and used to define a working volume, for example as explained below. "L" is the offset of the aim point of a sensor portion from the aim point of the sensor. Multiple aim points may be provided. In addition, a relatively continuous range of such points (e.g., as shown in FIG. 17A) may be used to define a distributed focus.

FIG. 17A is a schematic diagram showing multiple non-point focal aiming points for an alternative differential sensor 1700 in accordance with an exemplary embodiment of the invention.

In sensor 1700, a collimator 1704 comprises a plurality of slats which are arranged so that each pair of slats has a different aiming point, for example a series of points 1722 for a section 1710 of the sensor and a series of points 1720 for a section 1712 of the sensor. The main aiming point of the sensor as a whole is shown as 1714. As will be described below, one possible result of such spreading of aiming points is control over accuracy in the working volume of the sensor (e.g., dotted area 1416, FIG. 14). Typically, the width of the series of points 1722 and 1720 is smaller than the width of the collimator/detector (e.g., the whole detector or a single one of a pair or more than two detector sections of a sensor), for example, being less than 50%, less than 30%, less than 10%, or intermediate numbers.

In the example shown, while all the slats are angled inwards, for most of the slats, the angle is less than that of a comparable collimator (with focus at aiming point 1714).

Given, for example, a collimator (and sensor) design with the following properties (selected for a depth range of 20-40 cm and a maximum speed of 5 cm/sec):

a) Slat width: 1.5 mm
b) Slat height: 40 mm
c) Number of slats: 20
d) Spacing between slats: decreasing linearly from 1.5 mm at the center to 1 mm at the edges
e) Sensor depth: 23 mm
f) Focal distance: 400 mm With these collimator geometry parameters, in order to achieve a speed range up to 5 cm/sec at a distance of 20 cm, the slats can be set up so that each sensor section is aimed/focused at a maximum offset of 1 mm from the center line (e.g., left for the left section, right for the right section). If all slats are arranged for this type of focusing the accuracy at 20 cm is 0.32 mm and the accuracy at 40 cm is 1.6 mm.

In order to achieve a better than 1 mm accuracy at all distances within the range, accuracy at 40 cm should be improved. Optionally this is provided by readjusting the slats to achieve a defocusing effect, for example, leaving the center slats arranged for a 1 mm offset, and linearly increasing the focus offset distance up to 7 mm for the edge slats. This maintains the maximum speed of 5 cm/sec at 20 cm while improving the accuracy at 40 cm to 0.88 mm. The accuracy at 20 cm is slightly reduced to 0.36 mm. Non-linear changes in collimator parameters may be provided as well. Better accuracy can sometimes be achieved by also varying the slat heights. Series 1720 and/or 1722 optionally have a significant range of separation values, for example, 1 mm, 5 mm, 10 mm, 20 mm or smaller, intermediate or large values.

It should be noted that the graph of FIG. 15A is correct for a particular distance. At different distances, the accuracies change. Optionally, the spreading of focuses is used to control these accuracies. This generally lowers at least one of the static accuracy and dynamic accuracy. It is noted that a particular feature of some embodiments of the invention is that the behavior of the sensor is relatively uniform over a range of working distances, for example, the range 20-40 cm as in the example above.

Optionally, the distance of a source from the sensor is determined based on the sensitivity to angular motion (e.g., of the sensor, by sweeping). Often however, the opposite problem arises, that the mapping of signal to angle depends on the distance. Optionally, a plurality of tables matching signals to angles are provided for a plurality of distances (e.g., 10 or more distances). Optionally, a previous position of the tracked device and/or a position estimate provided by other sensors (e.g., 3 sensors may be used) provide at least an estimate of the distance and thus the table to use for angle estimation. Methods other than tables may be used, for example, analytical functions or neural networks.

Multiple aiming points may be provided for other reasons as well. In one example, a quadrant detector sensor is provided, in which each of a quadrant of the sensor is aimed/focused at a different x-y offset from a central aiming point, for example, one quadrant would be (+1, +1), another (+1, −1), and so on. This type of sensor may be used to detect a 2D angular offset of a source using a single detector.

In an exemplary embodiment of the invention, the angles of the slats are adjusted so as to allow adjusting the accuracy vs. the speed of the object. Optionally, individual ones of the signals generated by detector parts in the detector of FIG. 17A are used to determine what the effective focus of the detector will be and/or to shape signals 1502, 1504 and/or 1506 of FIG. 15A.

FIG. 17B is a schematic illustration of a sensor design in accordance with an exemplary embodiment of the invention.

As shown, sensor 1750 includes a frame 1752 on which are mounted two slotted plates 1754. A plurality of lead slats 1756 are arranged by the slots to create collimation for two sensor parts 1758 and 1760. The detectors associated with the sensor parts are optionally provided attached to the underside of frame 1752, for example an aluminum frame.

In an exemplary embodiment of the invention, the detectors are 2.5 cm×2.5 cm×10 cm in dimension and the collimator is 5 cm×10 cm, with maximum slat heights of 3.7 cm.

In an exemplary embodiment of the invention, an axis 1762 is provided for rotating frame 1752. Optionally, the axis is at a center of the detectors. Optionally, the detectors are curved, but this may not be meaningful at small angle changes and may adversely affect the uniformity of sensitivity of the detectors. Optionally, a motor 1764 is provided for rotating axis 1762.

Alternatively or additionally to rotation at the center of the detector and/or curving of the detector, compensation is made (e.g., in software) for changes in counts due to parts of the detector approaching or moving away from the source as the detector is rotated and/or due to the effective thickness of the detector. Optionally, these corrections are included in the above described look-up tables.

In an alternative design, the slats are connected by rotating pins (or other hinges) to the plates (not slotted) and the exact relative positions of the slats is determined by inserting a plastic (or other radio-transparent material) insert into the collimator, which plastic insert is a slotted plate machined (or cast) to have desirable relative slat angles. Optionally, not shown, one or more screws may be provided to adjust the slant angle relative to the slots of the plate or plastic insert.

FIG. 17C is a side view of sensor 1750, showing changes in slat heights.

Optionally, the center space between the detectors is used to house a light source, for example a collimated laser beam, used to indicate a position on a target.

Optionally, frame 1752 and/or plates 1754 are rounded, to conform to an optional cylindrical housing (not shown).

Figure 18:
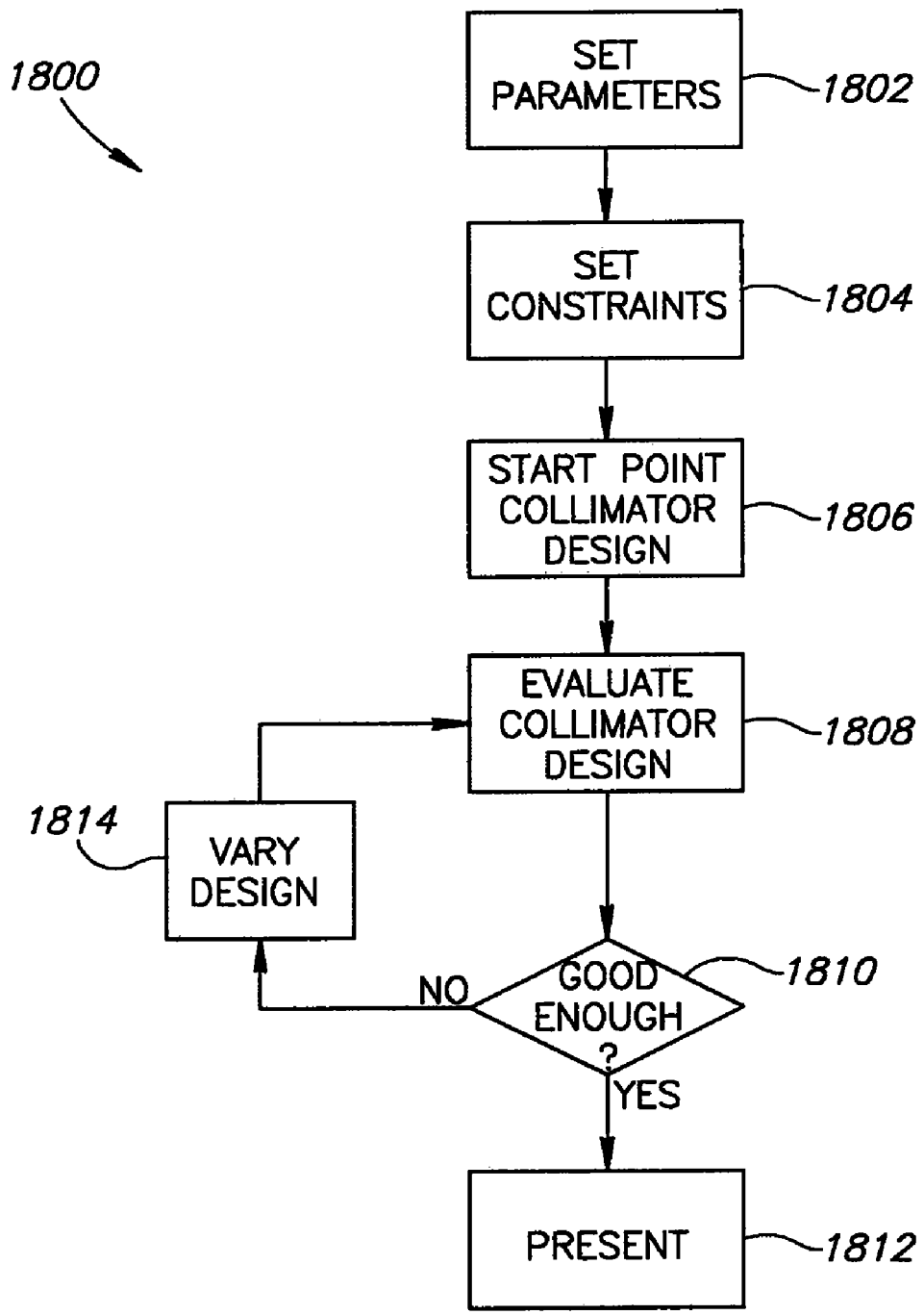
FIG. 18 is a flowchart of a method of collimator optimization and/or selection, in accordance with an exemplary embodiment of the invention.

FIG. 18 is a flowchart of a method of collimator optimization and/or selection, in accordance with an exemplary embodiment of the invention. As noted above, collimator/sensor design is, for example, an application specific compromise and may depend on the relative importance of lower latency during movement versus increasing accuracy when stationary (FIGS. 15B and 15C).

In the general method shown, at 1802 various parameters are set, for example, defining what the expected environment is. At 1804, various constraints (e.g., on parameters that vary during optimization) and/or desired quality thresholds or other indicators are set. At 1806, a starting point (e.g., collimator design) is selected.

At 1808, the current collimator design is evaluated. If it is good enough (1810), this collimator may be chosen (1812). Sufficiency of design may be determined in various manners, for example, based on certain design thresholds being met or based on lack of progress in the optimization process.

If the collimator was found lacking, the design is varied (1814) and this design is evaluated (1808).

Many optimization methods are known in the art and may be applied, for example, non-linear programming methods, hill climbing and/or exhaustive search.

Optionally, the performance of the collimator is evaluated by simulation. Alternatively or additionally, an analytical calculation is used, for example, based on optical assumptions regarding the radiation and collimator.

There are a number of collimator parameters which can be optimized through the selection of slat geometry. For simplicity of presentation, parameters other than the geometry of the collimator are assumed to be fixed. However, this need not be the case and such other parameters may play a part in optimization. These fixed parameters include, but need not be limited to sensor material and geometry, collimator slat material, and/or source energy and activity. In general, the optimization discussion will focus on slat thickness, placement, and height, which can all be different for each slat in the collimator. It is noted, however, that other geometrical properties can be modified, for example, slat shape (e.g., a trapezoid rather than a rectangle cross-section). For simplicity of simulation, variations in slat geometry were assumed to be limited to linear changes however, this is not essential and non-linear changes can be provided as well.

The various ranges of values within which a property is allowed to vary, are provided as an input to the optimization but may be changed, for example, the limits placed on the maximum height, minimum thickness, maximum geometrical resolution, will affect the optimization.

In an exemplary embodiment of the invention, the collimator design is optimized through the use of a simulator which simulates the differential sensor output versus source angle given the properties and geometries of the collimator and sensor. In an exemplary embodiment of the invention, the simulation first constructs a model of the sensors and collimators, and then calculates the signal output as follows:

1) for each of a series of source positions (angles relative to the sensor), the following procedure is followed:
   a) A large number of rays are defined, all starting at the source, and penetrating the sensor with uniformly distributed coverage.
   b) For each ray, the total length of collimator slat penetration is calculated, and the total length of sensor penetration is calculated.
   c) From the collimator slat and sensor penetration lengths, a value is calculated for the percentage of photons along that ray that would be recorded by the sensor.
   d) The number of photons per second represented by each ray is calculated based on the total number of photons given off by the source, the distance from the source, and the spacing of the rays.
   e) The percentage of photons recorded for each ray is averaged for all of the rays hitting a given sensor and then multiplied by the number of photons per second represented by each ray to obtain the simulated number of photons per second recorded by each sensor.
2) The number of photons recorded per second by each sensor is plotted for each of the source positions.
3) The numbers of photons recorded per second by each sensor are combined to obtain the differential sensor outputs for each source position. The differential output used for tracking is generally (a−b)/(a+b), where a and b are the signal outputs of the two sensors.

For the purpose of optimizing the collimator and sensor design, the value of a+b is optionally used as well, as it indicates the total number of photons per second recorded which can indicate the statistical accuracy with which the measured signal can be expected to match the theoretical signal.

The optimization of the collimator design is optionally achieved through an iterative minimization technique (1808-1814) in which a performance-related cost function is minimized by iteratively varying the geometric properties of the collimator, running the simulation, and assessing the performance.

It should be noted that for cases where a stationary source is to be localized, the static error may achieve a high importance (FIG. 15C). Optimization can be achieved for these cases by making the slats extremely thin and extremely close together and by making extremely small sensor rotations. In this way the jitter about the zero angle can be reduced to a minimum at the expense of very long latency when the source moves.

In cases where the source is moving the accuracy with which the source can be localized is important, however optimization of the system's dynamic response is generally desirable—minimizing the tracking error while the source is in motion. In the case of a moving source, due to the system's inherent response time, the source will not be at the zero angle at all times. As noted above, optionally the instantaneous location of the source at the time of measurement is calculated based on an estimate of the angle from the sensor to the source at the time of measurement.

In an exemplary embodiment of the invention, the system parameters (1802) used to define the requirements for the collimator in the case of a moving source include one or more of:

1) range of distances—this defines the minimum and maximum distance between the sensor and source for which the optimization should be performed.

2) maximum source speed—this defines the maximum speed of the source for which the dynamic accuracy should be considered (the maximum speed which the system needs to track accurately for a given tracking cycle, which may depend on the sensitivity of radiation detection). This value is given as the maximum movement of the source per measurement. In a perfect system, where a point source (rather than multiple sources) are viewed and knowing the refresh rate, this defines the angular range as well.

3) dynamic error—this defines the accuracy with which the sensor must estimate the current position of the source when at its maximum speed.

4) static error—this defines the accuracy with which the sensor must estimate the current position of the source when standing still.

5) optionally, system response speed which models an imperfect motion mechanism for the sensor, for example, including delay.

The range of distances and maximum source speed are absolute parameters that define the ranges of operation within which the optimization is performed. The dynamic and static error parameters are weights which define the relative importance of these parameters for a particular application. The algorithm uses these weights to trade off among these parameters in order to achieve an optimum collimator for the application.

For the purpose of describing the optimization methodology, a typical set of parameter values is chosen, but it should be clear that the values of these parameters are application dependant and they must be defined appropriately for every application.

For the application of tracking the position of the tip of a medical device within a patient's body the following system parameter values are used:
1) range of distances: 150-300 mm
2) maximum source speed: 5 mm/measurement (5 cm/sec, 10 Hz measurement rate)
3) dynamic error weight: 1
4) static error weight: 2

The geometrical parameters to be optimized can be selected and constrained (1804) based on the needed level of optimization and/or the collimator construction methods available. For the purpose of demonstrating the optimization methodology, a relatively simple set of parameters and constraints is selected:

Parameters which are allowed to vary:
1) slat thickness
2) slat height
3) slat spacing
4) collimator focal distance (the Y position of the focal point—its distance from the sensor)
5) collimator focal offset (the X position of the focal point—its distance from the zero plane/line of the sensor aiming)

Constraints:
1) minimum slat thickness: 1 mm
2) maximum slat height: 40 mm
3) geometrical resolution (accuracy to which thickness and spacing can be defined): 0.1 mm
4) thickness, height, and spacing of consecutive slats change linearly.
5) All slats on each half of the collimator are angled to focus on a single focal point located at the focal distance and focal offset. The slats in the two halves of the differential collimator will focus on different points, one with a positive offset from the zero plane, and one with a negative offset from the zero plane. As noted with respect to FIG. 17A, the angle may be varied between slats, for example, in a linear manner.

The actual parameters optimized by the optimization algorithm will generally depend upon the constraints. In this case, since the slat geometries are constrained to change linearly from slat to slat, each of the geometrical properties can be represented by two values, the value for the first slat and a linear factor to be applied to each consecutive slat. Since all slats on each half of the collimator are constrained to focus on a single focal point, the angles of all slats can be defined by two values; the focal distance and the focal offset. In this case there are 8 parameters to optimize:
1) first slat thickness
2) slat thickness linear factor
3) first slat height
4) slat height linear factor
5) first slat spacing
6) slat spacing linear factor
7) collimator focal distance
8) collimator focal offset The number of slats will be the number of slats that fit on the given sensor for each set of geometric parameter values.

In the above description, the movement of the source is assumed to be constant. Optionally, the simulation takes into account actual usage parameters. For example, the simulation may use a set or range of catheter motions and/or speeds, to compare collimator designs. Optionally, the simulation generates a quality for a collimator based on its overall behavior in a scenario or set of scenarios. For example, a first collimator may have a smaller average error but a greater maximum error than another design. However, if this maximum error is in a part of the path which is indicated as being less important and/or for limited conditions, the first design may be preferred.

Optionally, the simulation (e.g., source speed and/or paths) takes into account patient behavior (e.g., breathing and other natural body motion) and/or movement of the patient, for example, fidgeting.

Optionally, the optimization takes into account an angular range needed to be viewed at a same time, for example, to allow a detector to simultaneously receive signals from multiple radioactive sources on a single object (e.g., two sources with different energies on a same tool such as a catheter). Detection of the relative position of the sources is optionally used to determine an orientation of the tool.

Alternatively or additionally, the simulation can include a simulation of a tracking behavior by a modeled system, for example, with given tracking speed and/or tracking frequency. Optionally, such parameters of the system (e.g., tracking speed and/or frequency) are parameters which may be optimized by the simulation.

Optionally, detector design is part of the optimization, for example, including a parameter defining an accuracy of positional determination of a count within an area between two slats. This may be provided, for example, using a CCD array imager instead of a scintillation detector, to view the detector material (e.g., a doped halide crystal).

Optionally, for a given collimator/detector/system, a calibration envelope value (or set) is generated indicating maximum allowed speeds, angles, distance, etc. when, in actual use the envelope is exceeded or about to be exceeded, a user is optionally alerted. Optionally, a user can indicate a desired accuracy and the system will generate a warning when this desired accuracy cannot be achieved. Optionally, a calibration process is carried out where simulation results are normalized, for example, according to actual noise levels and/or source behavior.

In some cases, the application specific optimization takes into account time constraints. For example, even though a tracking algorithm is described, at some times, a scanning mechanism may be allowed. For example, the application may allow a user to pause a few times for a second or a fraction thereof (e.g., in response to a beep by the system) and allow the system to re-track.

It should be noted that while the above method can be used to generate an "optimal" or near optimal design for a collimator, optionally, the method is used to select from a set of available collimators.

Optionally, a set of collimators is provided, each one suitable for a different application and a software application or table is provided which matches up a best collimator with the application parameters. In an exemplary embodiment of the invention, a set of collimators includes between 4 and 10 collimators. Optionally, for a given application, 2-3 collimators are provided, for example, each one optimized for a different range of distances. In addition, applications may be loosely divided up into applications with very slow motion, intermediate speed (e.g., breathing motion) and high speed (e.g., catheter motion). Separate collimator sets may be provided for each such application. It should be noted that for high-speed detection of position, higher radioactivity may be desirable, than for low speeds.

Various collimators can be produced according to the methods described herein. In one example, the collimator is designed for a range of angles smaller than 150, 100, 80, or fewer milliradians. Alternatively or additionally, the collimator is designed for a range of angles of at least 5, at least 20, at least 30, at least 40, at least 50, or more or intermediate milliradians.

Alternatively or additionally, the collimator is designed for a range of depths, for example, at least 10 cm, at least 20 cm, at least 30 cm, at least 40 cm, at least 50 cm or intermediate values. Optionally, the collimator is designed for a range smaller than 100 cm, smaller than 80 cm, smaller than 50 cm or smaller than 30 cm. The width of the working volume is optionally similar to the depth range, but it may be greater, for example, being within 70%, 90% or smaller, intermediate or greater percentages of the detector length.

In an exemplary embodiment of the invention, the detector is smaller than 20 cm×20 cm or smaller than 10 cm×30 cm. Optionally, the working volume is within a ratio of 1:4 of the detector dimensions multiplied by the detector length. In an exemplary embodiment of the invention, the depth of the working volume is within a range of 1:10 of the width of the detector.

In an exemplary embodiment of the invention, the slope of the signal (1506) is stable to within a ratio of 1:1.5, 1:2, 1:3 or intermediate ratios over the working volume.

While multiple detector portions may be provided, optionally, the sensor is non-imaging. Optionally, the lack of imaging is inherent in the signal that is generated. Optionally, lack of imaging is provided by having fewer than 50, fewer than 20, fewer than 10 or intermediate numbers of separately read detector elements.

System 40 and/or sensors 20 rely upon execution of various commands and analysis and translation of various data inputs. Any of these commands, analyses or translations may be accomplished by software, hardware or firmware according to various alternative embodiments. In an exemplary embodiment of the invention, machine readable media contain instructions for transforming output signal 34 from one or more sensor modules 20 into position co-ordinates of source 38, optionally according to method 400. In an exemplary embodiment of the invention, CPU 42 executes instructions for transforming output signal 34 from one or more sensor modules 20 into position co-ordinates of source 38, optionally according to method 400.

According to an exemplary embodiment of the invention a trackable medical device is manufactured by incorporating into or fixedly attaching a detectable amount of a radioactive isotope to the medical device. The radioactive isotope may or may not have a medical function according to various embodiments. Optionally, the radioactivity of the isotope has no medical function. Optionally, the radioactive isotope may be selected so that it can be used in the body without a protective coating without adverse reaction with tissue. In an exemplary embodiment of the invention, the detectable amount of isotope is in the range of 0.5 mCi to 0.001 mCi. Use of isotope source 38 with an activity in the lower portion of this range may depend on lower speeds of the device, sensitivity of detector(s) 22, distance from sensor 20. Optionally, at least 1, optionally at least 5, optionally at least 10, optionally at least 100 detectable counts per second are produced by the incorporated radioactive isotope.

In the description and claims of the present application, each of the verbs "comprise", "include" and "have" as well as any conjugates thereof, are used to indicate that the object or objects of the verb are not necessarily a complete listing of members, components, elements or parts of the subject or subjects of the verb.

The present invention has been described using detailed descriptions of embodiments thereof that are provided by way of example and are not intended to necessarily limit the scope of the invention. The described embodiments comprise different features, not all of which are required in all embodiments of the invention. Some embodiments of the invention utilize only some of the features or possible combinations of the features. Variations of embodiments of the present invention that are described and embodiments of the present invention comprising different combinations of features noted in the described embodiments can be combined in all possible combinations including, but not limited to use of features described in the context of one embodiment in the context of any other embodiment. The scope of the invention is limited only by the following claims.

The invention claimed is:

1. An angle-responsive sensor, comprising:
   a radiation detector adapted to detect ionizing radiation;
   at least one collimator arranged to block radiation from reaching the detector in a manner dependent on a relative orientation of a radiation source, the detector and the collimator, the detector and the collimator defining an aim for the sensor; and
   circuitry coupled to the detector and which generates an output signal which varies as a function of the relative orientation,
   wherein the detector and the collimator are arranged to have a working volume of at least 10 cm in depth and having an angular width, such that the slope of the signal as a function of angle varies by less than a factor of 2 over the working volume.

2. The angle-responsive sensor of claim 1, wherein said signal is near linear over said working volume.

3. The angle-responsive sensor of claim 1, wherein said working volume has an angular range of at least 10 milliradians.

4. The angle-responsive sensor of claim 1, wherein said working volume has an angular range of at least 20 milliradians.

5. The angle-responsive sensor of claim 1, wherein said detector comprises at least two separate sections.

6. The angle-responsive sensor of claim 5, wherein circuitry generates said signal based on a combining of contributions of at least two separate sections of said radiation detector.

7. The angle-responsive sensor of claim 6, wherein said two sections each have different angular direction of maximum detection.

8. The angle-responsive sensor of claim 1, wherein said circuitry generates said signal for a source distance of at least 10 cm.

9. The angle-responsive sensor of claim 1, wherein said circuitry generates said signal for a source distance of at least 20 cm.

10. The angle-responsive sensor of claim 1, wherein said working volume has a range of depths having a ratio of at least 1:2.

11. The angle-responsive sensor of claim 5, wherein the detector comprises two sections, each one with a different focal area.

12. The angle-responsive sensor of claim 5, wherein said collimator provides multiple focal points for each of said sections.

13. The angle-responsive sensor of claim 5, wherein said collimator allows wide angle radiation at a spatial angle of at least 10 degrees for at least two sections.

14. The angle-responsive sensor of claim 5, wherein a focal point of a first section is distanced from a focal point of a second section in a direction parallel to said detector, a distance of at least 1 mm.

15. The angle-responsive sensor of claim 14, wherein the detector comprises additional sections with additional focal points distanced along said parallel direction.

16. The angle-responsive sensor of claim 14, wherein the sensor has a relatively linear angular response over an angle range of at least 10 milliradians.

17. The angle-responsive sensor of claim 14, wherein said sensor has a relatively linear angular response over a depth range of at least 10 cm.

18. The angle-responsive sensor of claim 5, comprising fewer than 50 separately read detector sections.

19. The angle-responsive sensor of claim 18, comprising fewer than 20 separately read detector sections.

20. The angle-responsive sensor of claim 19, comprising fewer than 10 separately read detector sections.

* * * * *